(12) United States Patent
Jha et al.

(10) Patent No.: US 10,135,849 B2
(45) Date of Patent: Nov. 20, 2018

(54) SECURING MEDICAL DEVICES THROUGH WIRELESS MONITORING AND ANOMALY DETECTION

(71) Applicants: Niraj K. Jha, Westfield, NJ (US); Anand Raghunathan, West Lafayette, IN (US); Meng Zhang, Princeton, NJ (US)

(72) Inventors: Niraj K. Jha, Westfield, NJ (US); Anand Raghunathan, West Lafayette, IN (US); Meng Zhang, Princeton, NJ (US)

(73) Assignees: PURDUE RESEARCH FOUNDATION, West Lafayette, IN (US); THE TRUSTEES OF PRINCETON UNIVERSITY, Princeton, NJ (US)

( * ) Notice: Subject to any disclaimer, the term of this patent is extended or adjusted under 35 U.S.C. 154(b) by 85 days.

(21) Appl. No.: 13/839,768

(22) Filed: Mar. 15, 2013

(65) Prior Publication Data

US 2013/0247194 A1 Sep. 19, 2013

Related U.S. Application Data

(60) Provisional application No. 61/612,081, filed on Mar. 16, 2012.

(51) Int. Cl.
*H04L 29/06* (2006.01)
*H04W 12/12* (2009.01)
(Continued)

(52) U.S. Cl.
CPC ........ *H04L 63/1425* (2013.01); *A61B 5/0022* (2013.01); *G06F 19/00* (2013.01);
(Continued)

(58) Field of Classification Search
CPC ....... H04N 7/16; G06F 11/30; H04L 63/1425; H04L 29/06; A61B 5/0022; A61B 5/14532; H04W 12/12
(Continued)

(56) References Cited

U.S. PATENT DOCUMENTS 8,561,177 B1* 10/2013 Aziz et al. ...................... 726/22
2004/0162995 A1* 8/2004 Muaddi ............... H04L 63/1408
726/23
(Continued)

OTHER PUBLICATIONS

D. Arney, K. Venkatasubramanian, O. Sokolsky, and I. Lee, "Biomedical devices and systems security," in Proc. IEEE Int. Conf. Engg. in Medicine and Biology Society, Sep. 2011, pp. 2376-2379.
(Continued)

*Primary Examiner* — Ashokkumar B Patel
*Assistant Examiner* — Quazi Farooqui
(74) *Attorney, Agent, or Firm* — Meagher Emanuel Laks Goldberg & Liao, LLP

(57) ABSTRACT

A medical device monitor (MedMon), method and computer readable medium is disclosed. The MedMon is configured to operate in a system having communications between a first medical device associated with a patient and a second device. The MedMon includes a receiver configured to snoop on communications between the first medical device and second device. An anomaly detector having a set of security polices is configured to detect an anomaly by analyzing the communications between the first medical device and second device for compliance with the security policies. A response generator configured to generate a response on a condition that an anomaly is detected. The response may be a warning message configured to warn the patient. The MedMon may include a transmitter configured to transmit the response. The response may be a jamming
(Continued)

signal configured to disrupt communications between the first medical device and second device.

21 Claims, 14 Drawing Sheets

(51) Int. Cl.
```
A61B 5/00      (2006.01)
G06F 19/00     (2018.01)
G16H 40/67     (2018.01)
A61B 5/145     (2006.01)
```
(52) U.S. Cl.
CPC ............ *G16H 40/67* (2018.01); *H04W 12/12* (2013.01); *A61B 5/14532* (2013.01)
(58) Field of Classification Search
USPC .......................... 726/22–23, 25, 32; 713/186
See application file for complete search history.

(56) References Cited

U.S. PATENT DOCUMENTS

| | | | |
|---|---|---|---|
| 2007/0094741 A1* | 4/2007 | Lynn | .................. H04L 41/0893 726/26 |
| 2011/0145894 A1* | 6/2011 | Garcia Morchon | ........................ G06F 19/3418 726/4 |

OTHER PUBLICATIONS

D. Halperin et al., "Pacemakers and im-plantable cardiac defibrillators: Software radio attacks and zero-power defenses" in Proc. IEEE Symp. Security and Privacy, May 2008, pp. 129-142.
C. Li, A. Raghunathan, and N. K. Jha, "Hijacking an insulin pump: Security attacks and defenses for a diabetes therapy system," in Proc. IEEE Int. Conf. e-Health Networking, Applications and Services, Jun. 2011.
C. Purvis, "Implantable medical devices: Hacks and countermeasures," Aug. 2011, http://www.securitymanagement.com/news/.
D. L. Hayes, P. Wang, D. W. Reynolds, E. Mark, J. L. Griffith, R. A. Steffens, G. L. Carlo, G. K. Findlay, and C. M. Johnson, "Interference with cardiac pacemakers by cellular telephones," N. England J. Medicine, vol. 336, No. 21, pp. 1473-1479, May 1997.
C. Jilek, S. Tzeis, T. Reents, H.-L. Estner, S. Fichtner, S. Ammar, J. Wu, G. Hessling, I. Deisenhofer, and C. Kolb, "Safety of implantable pacemakers and cardioverter defibrillators in the magnetic field of a novel remote magnetic navigation system," J. Cardiovascular Electrophysiology, vol. 21, No. 10, pp. 1136-1141, Oct. 2010.
J. M. Bronstein et al., "Deep brain stimulation for Parkinson disease: An expert consensus and review of key issues," Arch. Neurol., vol. 68, No. 2, pp. 165-171, Feb. 2011.
W. Theodore and R. Fisher, "Brain stimulation for epilepsy," Lancet Neurol., vol. 3, No. 2, pp. 111-118, Feb. 2004.
A. Csavoy, G. Molnar, and T. Denison, "Creating support circuits for the nervous system: Considerations for brain-machine interfacing," in Proc. Int. Symp. VLSI Circuits, Jun. 2009, pp. 4-7.
I. Lee, G. Pappas, R. Cleaveland, J. Hatcliff, B. Krogh, P. Lee, H. Rubin, and L. Sha, "High-confidence medical device software and systems," Computer, vol. 39, No. 4, pp. 33-38, Apr. 2006.
Android, "Infected apps found in Google's Android market," 2011, http://www.securitynewsdaily.com.
P. Kocher, J. Jaffe, and B. Jun, "Differential power analysis," in Proc. Int. Cryptology Conf., Aug. 1999, pp. 388-397.
P. Kocher, "Timing attacks on implementations of Diffie-Hellman, RSA, DSS, and other systems," in Proc. Int. Cryptology Conf., vol. 1109, Aug. 1996, pp. 104-113.
D. Agrawal, B. Archambeault, and J. R. Rao, "The EM side-channel(s)," in Proc. Workshop Cryptographic Hardware and Embedded Systems, Aug. 2002, pp. 29-45.

J. Chen, K. Kwong, D. Chang, J. Luk, and R. Bajcsy, "Wearable sensors for reliable fall detection," in Proc. IEEE Int. Conf. Engineering in Medicine and Biology Society, Jan. 2005, pp. 3551-3554.
T. Martin, M. Hsiao, D. Ha, and J. Krishnaswami, "Denial-of-service attacks on battery-powered mobile computers," in Proc. IEEE Conf. Pervasive Computing and Communications, Mar. 2004, pp. 309-318.
L. Schwiebert, S. Gupta, P. Auner, G. Abrams, R. Iezzi, and P. McAllister, "A biomedical smart sensor for the visually impaired," in Proc. IEEE Sensors, vol. 1, Nov. 2002, pp. 693-698.
K. D. Daniel, G. Y. Kimb, C. C. Vassiliou, M. Galindo, A. R. Guimaraes, R. Weissleder, A. Charest, R. Langer, and M. J. Cima, "Implantable diagnostic device for cancer monitoring," Biosens. Bioelectron., vol. 24, No. 11, pp. 3252-3257, Jul. 2009.
C. Israel and S. Barold, "Pacemaker systems as implantable cardiac rhythm monitors," American J. Cardiology, vol. 88, No. 4, pp. 442-445, Aug. 2001.
K. Fotopoulou and B. Flynn, "Optimum antenna coil structure for inductive powering of passive RFID tags," in Proc. IEEE Int. Conf. RFID, Mar. 2007, pp. 71-77.
G. P. Hancke and S. C. Centre, "Eavesdropping attacks on high-frequency RFID tokens," in Proc. Workshop RFID Security, Jul. 2008, pp. 100-113.
E. Haselsteiner and K. Breitfuss, "Security in near field communication," in Proc. Workshop RFID Security, Jul. 2006, pp. 3-13.
H. Baldus, S. Corroy, A. Fazzi, K. Klabunde, and T. Schenk, "Human-centric connectivity enabled by body-coupled communications," Comm. Mag., vol. 47, pp. 172-178, Jun. 2009.
K. B. Rasmussen, C. Castelluccia, T. S. Heydt-Benjamin, and S. Capkun, "Proximity-based access control for implantable medical devices," in Proc. ACM Conf. Computer and Communications Security, Nov. 2009, pp. 410-419.
S. Schechter, "Security that is meant to be skin deep: Using ultraviolet micropigmentation to store emergency-access keys for implantable medical devices," Microsoft Research, Tech. Rep. MSR-TR-2010-33, Apr. 2010.
F. Xu, Z. Qin, C. Tan, B. Wang, and Q. Li, "IMDGuard: Securing implantable medical devices with the external wearable guardian," in Proc. IEEE Int. Conf. Computer Communications, Apr. 2011, pp. 1862-1870.
T. Denning, K. Fu, and T. Kohno, "Absence makes the heart grow fonder: New directions for implantable medical device security," in Proc. Conf. Hot Topics in Security, Jul. 2008, pp. 1-7.
S Gollakota, H. Hassanieh, B. Ransford, D. Katabi, and K. Fu, "They can hear your heartbeats: Non-invasive security for implantable medical devices," in Proc. ACM Conf. Special Interest Group on Data Communication, Aug. 2011.
W. Moore, "A review of fault-tolerant techniques for the enhancement of integrated circuit yield," Proc. IEEE, vol. 74, No. 5, pp. 684-698, May 1986.
B. Randell, "System structure for software fault tolerance," SIGPLAN Not., vol. 10, pp. 437-449, Apr. 1975.
R. E. Lyons and W. Vanderkulk, "The use of triple-modular redundancy to improve computer reliability," IBM J. Res. Dev., vol. 6, pp. 200-209, Apr. 1962.
D. Arney, R. Jetley, P. Jones, I. Lee, and O. Sokolsky, "Formal methods based development of a PCA infusion pump reference model: Generic infusion pump (GIP) project," in Proc. Joint Workshop High Confidence Medical Devices, Software, and Systems and Medical Device Plug-and-Play Interoperability, Jun. 2007, pp. 23-33.
K. Sandler, L. Ohrstrom, L. Moy, and R. McVay, "Killed by code: Software transparency in implantable medical devices," 2010, http://www.softwarefreedom.org.
R. Jetley, S. Iyer, P. Jones, and W. Spees, "A formal approach to pre-market review for medical device software," in Proc. Int. Conf. Computer Software and Applications, Sep. 2006, pp. 169-177.
L. Cordeiro, B. Fischer, H. Chen, and J. Marques-Silva, "Semiformal verification of embedded software in medical devices considering stringent hardware constraints," in Proc. IEEE Int. Conf. Embedded Software and Systems, May 2009, pp. 396-403.
C. M. Holloway, "Why engineers should consider formal methods," in Proc. IEEE Digital Avionics Systems Conf., Oct. 1997, pp. 16-22.

(56) References Cited

OTHER PUBLICATIONS

S. W. Smith and S. Weingart, "Building a high-performance, programmable secure coprocessor," Comput. Netw., vol. 31, pp. 831-860, Apr. 1999.
"Intel trusted execution technology (TXT)," http://www.intel.com /technology/malwarereduction/index.htm., 2012.
"ARM trustzone technology overview," http://www.arm.com/products/CPUs/arch-trustzone.htm., 2009.
C. Li, A. Raghunathan, and N. K. Jha, "Secure virtual machine execution under an untrusted management OS," in Proc. IEEE Int. Conf. Cloud Computing, Jul. 2010, pp. 172-179.
N. Aaraj, A. Raghunathan, and N. K. Jha, "Analysis and design of a hardware/software trusted platform module for embedded systems," ACM Trans. Embed. Comput. Syst., vol. 8, pp. 8:1-8:31, Jan. 2009.
V. Chandola, A. Banerjee, and V. Kumar, "Anomaly detection: A survey," ACM Comput. Surv., vol. 41, pp. 15:1-15:58, Jul. 2009.
N. Patwari, J. N. Ash, S. Kyperountas, A. O. Hero III, R. L. Moses, and N. S. Correal, "Locating the nodes: Cooperative localization in wireless sensor networks," IEEE Signal Processing Magazine, vol. 22, No. 4, pp. 54-69, Jul. 2005.
G. Sun, J. Chen, W. Guo, and K. Liu, "Signal processing techniques in network-aided positioning: A survey of state-of-the-art positioning designs," Signal Processing Magazine, IEEE, vol. 22, No. 4, pp. 12-23, Jul. 2005.

\* cited by examiner

SECURING MEDICAL DEVICES THROUGH WIRELESS MONITORING AND ANOMALY DETECTION

CROSS-REFERENCE TO PRIOR FILED APPLICATIONS

This application claims priority to earlier filed provisional application 61/612,081 which was filed on Mar. 16, 2012, incorporated herein in its entirety.

STATEMENT REGARDING FEDERALLY SPONSORED RESEARCH OR DEVELOPMENT

This invention was made with government support under Grant no. CNS0914787 awarded by the National Science Foundation. The government has certain rights in the invention.

FIELD OF INVENTION

The present disclosure generally relates to medical devices, and in particular to systems and processes for securing medical devices.

BACKGROUND

Rapid advances in personal healthcare systems based on implantable and wearable medical devices promise to greatly improve the quality of diagnosis and treatment for a range of medical conditions. However, the increasing programmability and wireless connectivity of medical devices also open up opportunities for malicious attackers. Unfortunately, implantable/wearable medical devices come with extreme size and power constraints, and unique usage models, making it infeasible to simply borrow conventional security solutions such as cryptography.

In recent years, medical advances as well as innovations in ultra low-power computing, networking, and sensing technologies have led to an explosion in implantable and wearable medical devices (IWMDs). IWMDs are currently used to perform cardiac pacing, defibrillation, insulin delivery and glucose monitoring, deep brain stimulation, intrathecal drug infusion, and many other diagnostic, monitoring, and therapeutic functions. IWMDs commonly include wireless communication interfaces through which they can be connected to external diagnostic or programming equipment through, or to body area networks (BANs) to form personal healthcare systems (PHSs). A Personal Healthcare System (PHS) typically includes sensors for physiological data collection, actuators for therapy delivery, remote controllers for reconfiguration, and a hub for logging, compressing, and analyzing the raw health data.

Since the functions performed by IWMDs and PHSs are frequently life-critical, any malfunction in their operation is of utmost concern. An incessant trend in IWMDs has been towards increased functional complexity, software programmability, and network connectivity. While these advances are desirable from the viewpoint of the improvements that they engender in diagnostic/therapeutic effectiveness and convenience to patients, they also collude to greatly increase the risk of security vulnerabilities and malicious attacks. Ensuring the security of IWMDs and PHSs is a sine qua non since the functions that they perform are frequently life-critical, e.g., cardiac pacing, continuous blood glucose monitoring and insulin delivery (CBGM) and brain-machine interfacing (BMI). Unfortunately, the very tight power and size budgets that are inherent to IWMDs virtually rule out the use of conventional security solutions such as cryptography. Inductive charging offers the possibility of relaxing the energy constraints and avoiding the complications and costs associated with replacing batteries for medical implants. However, wireless charging for IWMDs is still in the research phase and must go through rigorous testing to ensure safety before commercial use. In addition to resource constraints, the need for emergency responders to communicate with medical devices (in the absence of any mechanism, such as public key infrastructure, for shared key establishment) is also cited as a factor preventing the use of encryption. In summary, the current generation of IWMDs typically does not employ cryptographic protection for their radio-frequency (RF) wireless communications.

Due to the absence of cryptographic protection, the wireless channel has been identified as the Achilles' heel of medical devices. Recent demonstrations of successful RF wireless attacks on cardiac pacemakers and insulin pumps have placed medical device security under great scrutiny. For example, an attack described on a glucose monitoring and insulin delivery system may exploit the wireless channels between the device and controller, and between medical devices. In such a scenario, the attacker first eavesdrops on the wireless packets sent from a remote control to an insulin pump. From the captured packets, the attacker reverse-engineers the device PINs associated with the remote control and glucose meter. By mimicking the remote control, the attacker can configure the insulin pump to disable or change the intended therapy, stop the insulin injection, or inject a much higher dose than allowed. By mimicking the glucose meter, the attacker can send bogus data to the insulin pump, causing the pump to adjust insulin delivery based on the false data. In addition, the attacker can snoop on the packets to infer sensitive patient data.

The above attack is hard to defend against, especially because it is hard to differentiate the attacker's forged wireless transmissions from legitimate ones. It would be desirable to provide improved a medical security monitor that detects such wireless attacks and protects PHS integrity and patient safety.

SUMMARY OF THE INVENTION

A medical device monitor (MedMon), method and computer readable medium is disclosed. The MedMon is configured to operate in a system having communications between a first medical device associated with a patient and a second device. The MedMon includes a receiver configured to snoop on communications between the first medical device and second device. An anomaly detector having a set of security polices is configured to detect an anomaly by analyzing the communications between the first medical device and second device for compliance with the security policies. A response generator configured to generate a response on a condition that an anomaly is detected. The response may be a warning message configured to warn the patient. The MedMon may include a transmitter configured to transmit the response. The response may be a jamming signal configured to disrupt communications between the first medical device and second device.

The anomaly detector may be configured to detect physical anomalies based on a security policy including a physical characteristic of the transmitted signal including at least one of: signal strength indicator (RSSI), time of arrival (TOA), differential time of arrival (DTOA), and angle of arrival (AOA). The MedMon may include a memory that is configured to store historical information including communications between the first medical device and second device. The anomaly detector may be configured to detect behavioral anomalies based on a security policy including a behavioral characteristic of the transmitted signal. Each security policy may be associated with a specific anomaly and has an associated response that is selected on a condition that the specific anomaly is detected.

A method of monitoring communications between a first medical device associated with a patient and a second device is disclosed. The method includes snooping on communications between the first medical device and second device. The method also includes detecting an anomaly by analyzing the communications between the first medical device and second device for compliance with at least one security policy. The method also includes generating a response on a condition that an anomaly is detected. The response may be a warning message configured to warn the patient. The method may include transmitting the response. The response may be a jamming signal configured to disrupt communications between the first medical device and second device. The method may also include detecting physical anomalies based on a security policy including a physical characteristic of the transmitted signal including at least one of: signal strength indicator (RSSI), time of arrival (TOA), differential time of arrival (DTOA), and angle of arrival (AOA).

The method may also include storing in a memory historical information including data and commands transmitted between the first medical device and second device. The method may also include detecting behavioral anomalies based on a security policy including a behavioral characteristic of the transmitted signal. Each security policy may be associated with a specific anomaly and have an associated response that is selected on a condition that the specific anomaly is detected.

BRIEF DESCRIPTION OF THE FIGURES

FIG. 6b is a graph showing the intercepted and down-converted wireless signals sent by the remote control in FIG. 6a.

DETAILED DESCRIPTION OF THE INVENTION

Figure 1:
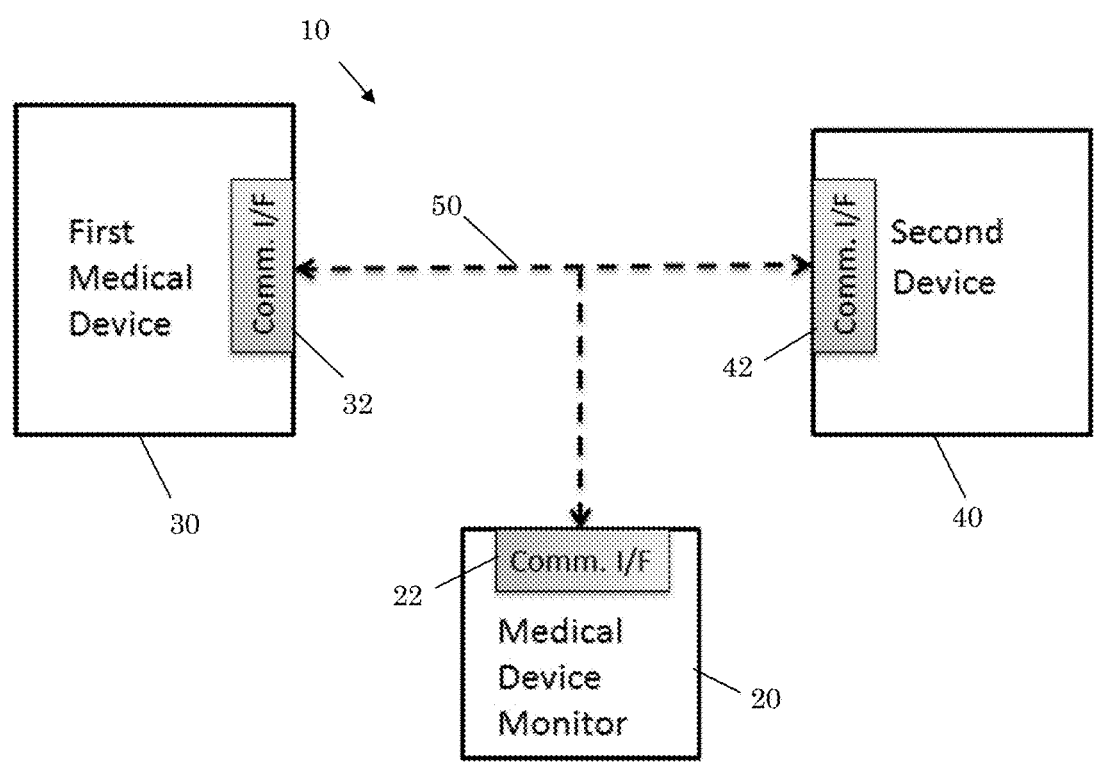
FIG. 1 is a block diagram of a system including the medical device security monitor (MedMon)

Disclosed herein is a medical device security monitor (MedMon) that detects wireless attacks and protects PHS integrity and patient safety. The MedMon is based on the observation that although the attacker's transmissions may conform to the communication protocol, they are likely to deviate from legitimate transmissions either in the physical signal characteristics or in the behavior or underlying content. The MedMon is an external monitor that tracks all wireless communications to/from medical devices and identifies potentially malicious transactions using multi-layered anomaly detection. When anomalies are captured, the MedMon can warn the patient and jam the suspicious transmission before it changes the state of the target device. The MedMon can be implemented in a variety of configurations such as a dedicated device or built into an existing personal device such as a smartphone. The MedMon may be implemented in a truly non-invasive fashion. For example, hardware or software modifications in existing medical devices are not required. The MedMon may be used in a variety of applications. Also disclosed herein is an implementation for a glucose monitoring and insulin delivery system, where the MedMon is used to prevent a wide range of wireless attacks. The MedMon addresses what is believed to be the most pressing issue in medical device security, namely the loss of integrity that may result in endangerment of a patient's health or life.

Threat and Risk Analysis

Threat Analysis

A variety of threats can potentially compromise a PHS and make its operation outside of its intended parameters. These threats may arise from hardware/software errors as well as malicious attacks, including wireless attacks, side-channel attacks, malware attacks and vulnerability exploits.

Hardware Failures

In general, a hardware failure can be in electronic or non-electronic components. Examples of non-electronic hardware failure include contaminated syringes and broken wheelchairs. Electronic hardware failure can be caused by undetected manufacturing defects, wear-and-tear faults due to electromigration, hot carrier degradation, dielectric breakdown, etc., as well as transient errors caused by the complex physical environment (e.g., noise, power disturbance, extreme temperature, vibration, electromagnetic interference, etc.). Studies have shown that electromagnetic interference may cause temporary or permanent malfunction in pacemakers and implantable cardioverter defibrillators (ICDs).

Many medical devices perform life-sustaining functions, such as cardiac pacing and defibrillation, insulin delivery and administration. They are also responsible for monitoring, recording and storing private patient information, and making changes in response to doctors' orders. The functionalities and the fact that the implanted devices are in close contact with human organs leave zero error space for hardware failure. A glitch on a cellphone may go unnoticed, whereas a glitch on a pacemaker or an ICD can be life-threatening.

Besides cardiovascular and diabetic devices, neuromodulation devices that treat neurological conditions, such as Parkinson's disease and epilepsy, are also examples that call for high standards for robustness and reliability. In a typical deep-brain stimulation system offered by Medtronic, several leads with electrodes are implanted in the brain and connected to a neurostimulator implanted near the clavicle. The amount of electrical stimulation can be non-invasively adjusted by a programmer. However, electromagnetic interference, if strong enough, could also change the parameter values of the neurostimulator, turn the neurostimulator off, or cause it to jolt the patient.

A brain-machine interface (BMI) is considered to be the heart of the next generation of neuromodulation devices. It is a direct communication pathway between the brain and an external device. BMI studies have shown promise in memory augmentation as well as perceptual and motor prostheses. However, in addition to the technical challenges posed by interfacing of silicon with neurons, reliability concerns remain. Whether BMI can reliably interact with the complex nervous system without being disrupted by environmental interferences needs further study.

Software Errors

Many medical devices are essentially embedded systems and have software content. Any safety and regulatory requirements for medical devices necessarily call for a rigorous software development process and skilled engineers in order to minimize software errors and protect public health. Unfortunately, designing bug-free software is difficult, especially for complex devices that might be used in unanticipated contexts. For example, during execution, a software program often requests a certain amount of memory space to store data values. If the program does not perform boundary checks properly, it may inadvertently write more data to the memory than what the designated memory space can hold. As a result, the adjacent block of memory is overwritten, and data stored there corrupted. This is called a buffer overflow, and is a common cause of software vulnerability. Buffer overflows and other software errors do not necessarily manifest themselves during the development and testing phases and may result in errors after deployment. Comprehensive system testing is possible for the simplest systems. As medical systems become more "intelligent" and thus more complex, testing alone is not sufficient for gaining confidence in the system.

Wireless Attacks

Figure 3:
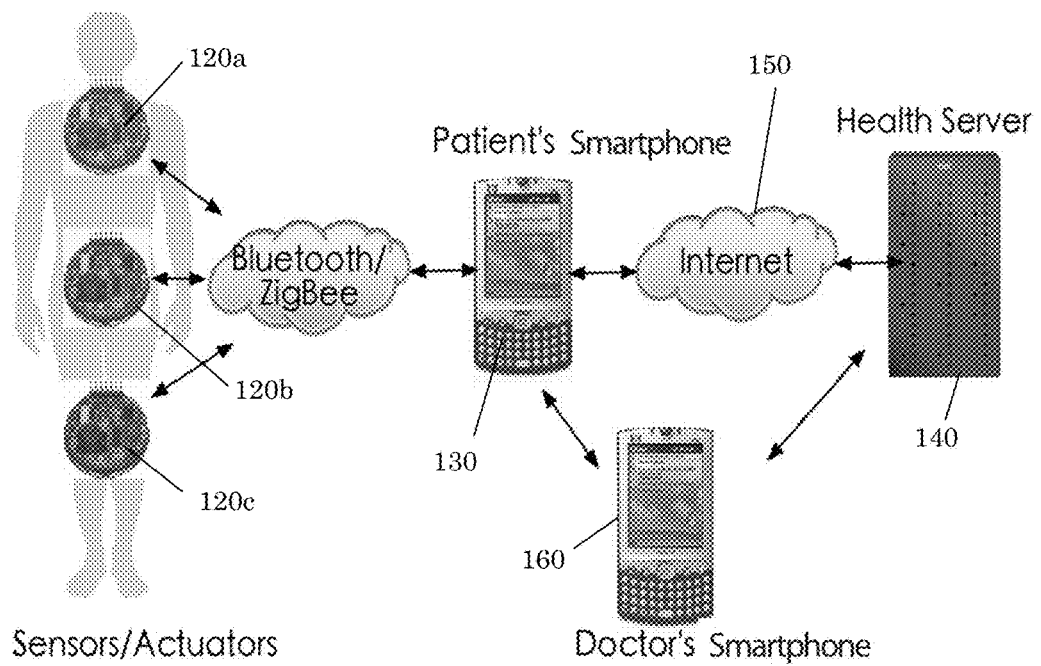
FIG. 3 is block diagram showing a generic architecture of a personal healthcare system.

Since often no cryptographic protection is employed, wireless channels between devices and external controllers, e.g., the link between sensors/medical devices 120a-120c and the personal digital assistant (PDA) 130 in FIG. 3, and between other medical devices that communicate with each other, are highly prone to attacks.

Besides the wireless attack on a glucose monitoring and insulin delivery systems, another successful wireless attack on an ICD have been demonstrated. The research shows how the ICD's design involving wireless communication with an external programmer can be exploited by an attacker. By reverse-engineering the communication protocol, the attacker can launch wireless attacks, with consequences ranging from disclosure of private data to alteration of device settings. In the worst case, the attacker can maliciously reconfigure the ICD to harm a patient by inaction (failure to deliver treatment when necessary) or by delivering an electrical stimulus when the heart is beating normally.

With the knowledge of the communication protocol, denial-of-service attacks that aim to drain an IWMD's battery power may be launched through the wireless channel. If the IWMD responds to each incoming communication request from attackers, its battery may simply die out soon and need to be surgically replaced. In addition, an attacker could also generate a large amount of noise to jam normal communication if he simply knows the approximate frequency of transmissions.

Malware and Vulnerability Exploits

Various forms of malware, including viruses, worms, Trojans, keyloggers, botnets, and rootkits, have emerged and keep evolving and adapting to new platforms. Smartphone platforms, such as Symbian and Android, have been breached by mobile malware. With the increasing flexibility and connectivity of PHS platforms, it is just a matter of time before the first appearance of malware that targets PHS platforms.

For example, Intel Health Guide is a chronic care product that delivers personalized health monitoring at home. Patients can use the system to measure their own vital signs and, through the Internet, upload the results to a remote server, where healthcare professionals can assess the patient's health condition. A virus that infects such a system can delete or forge health data.

Furthermore, since software is inherently complex, abstract and intangible, software vulnerabilities are inevitable and difficult to detect. In an incident of buffer overflow, the corrupted memory could originally be holding an address to an instruction, which the program should be redirected to. After corruption of the address, the program may be redirected to a false address and start executing random code. If a buffer overflow is triggered by especially-crafted user inputs, causing the redirected program to execute malicious code, it is called a buffer overflow attack. With some knowledge of system software, attackers can exploit the buffer overflow vulnerabilities as well as other software vulnerabilities to steal private information, tamper with medical data and even change device settings.

Side-channel Attacks

Side-channel attacks employ statistical analysis of information leaked through physical channels, such as power consumption, execution time, electromagnetic emission, etc. Side-channel attacks can possibly be used against PHSs and medical devices for privacy invasion. Other attack scenarios are possible as well. Suppose communications between implanted pacemakers and external programmers are encrypted, and the same secret key is shared by substantially all pacemakers of the same model so that the ambulance staff can access the device in case of an emergency. If an attacker has access to a pacemaker unit, the secret key can become a vulnerable target for differential power analysis, a form of side-channel attack that utilizes power consumption information. Once successful, the attacker could reveal and publicize the secret key and thus make the cryptographic protection ineffectual.

Intel Health Guide system is equipped with integrated cameras, allowing on-line health sessions and video consultations through the Internet. However, the network traffic flow may leak patients' private information. The schedule of health sessions and video calls, for example, could be deduced from monitoring the network traffic flow. One could also infer a change in the patient's health condition, if the lengths and frequencies of health sessions and video calls suddenly increase.

Risk Analysis

A PHS that is impacted by attacks or malfunctions can lead to different types of risks. Ensuring the safety of PHSs involves protection against each type of potential risk. PHS security shares the high-level goals of traditional information security: confidentiality, integrity and availability. In addition, privacy is another useful goal for PHSs and medical devices. Privacy involves keeping the presence of the device on the patient confidential. Correspondingly, a PHS can be subject to four types of potential risks: confidentiality, integrity, availability, and privacy.

Confidentiality Risk

Confidentiality refers to the ability to secure private data or information from access by unauthorized parties. The confidentiality risk level is high if leaked data are of great importance or can compromise patient privacy. For example, the glucose monitoring and insulin delivery system in effectively broadcasts the patient's diabetic condition when wirelessly transmitting unencoded data and commands.

Integrity Risk

Integrity means that the information transmitted between devices is authentic and complete. Integrity is at risk when the transmitted information is altered due to malfunctions or attacks. Depending on the device functionality, the consequence of an integrity compromise can be catastrophic, e.g., an ICD whose setting is changed by an attacker. If the device monitors the patient condition and does not provide direct treatment, but the treatment is decided based on the monitored data, corrupted data may also lead to unsafe therapy. In these cases, the integrity risk level is high. If the device only provides monitoring capability and treatment is decided based on further assessment, the result may not necessarily be harmful. For example, the wearable fall detector for the elderly detects the occurrence of an unintentional fall and provides the location of the victim. A malfunctioning detector may repeatedly send false alarms when the patient is safe and sound. In this case, although the responder may be annoyed, the detector can be easily replaced. Therefore, the integrity risk level is low, as patient safety is not affected.

Availability Risk

Availability refers to the assurance that the PHS is available when needed. Availability risk implies that the PHS may stop functioning due to attacks, hardware/software error, low battery, etc. Battery-draining attacks, a form of denial-of-service attack, are in some embodiments aimed at causing unavailability. Evidently, the availability risk associated with devices that perform life-sustaining functions is high. For other devices, inaction can cause catastrophic consequence in indirect ways. For example, a visually-impaired person aided by an artificial retina prosthesis can suddenly lose vision while driving or crossing the street due to retina sensor failure.

Privacy Risk

In the context of this disclosure, privacy refers to the ability to hide the patient's condition from unauthorized parties. Privacy risk implies that using a PHS or carrying a device may disclose the patient's illness. While a wheelchair user may not expect some privacy, it is understandable if a cancer patient wearing a tumor monitor prefers to keep his condition a secret. With the help of X-ray cameras, metal sensors, electromagnetic sensors, etc., it is possible for attackers to identify less obvious or even implanted devices.

If the attacker has knowledge of the wireless communication protocol used, the communication between a medical device and another easily reveals its presence. So does a response to a communication request sent by an attacker. Examples of several PHSs and their associated threats and risks are listed in Table I.

TABLE I

THREATS AND RISKS IN PHSs

| System/Device | Threat | Risk |
| --- | --- | --- |
| Pacemaker and ICD | software/hardware error | I, A |
| | side-channel attack | C, I, A, PC, I, A, P |
| Insulin pump | software/hardware error | I, A C, P |
| | side-channel attack | C, I, A, P |
| Deep brain stimulation | software/hardware error | I, A C, P |
| | side-channel attack | C, I, A, P |
| Intrathecal drug delivery | software/hardware error | I, A C, P |
| | side-channel attack | C, I, A, P |
| Retina sensor | software/hardware error | I, A |
| Cochlear implant | software/hardware error | I, A |
| Fall detector | software/hardware error | I, A |
| | wireless attack | C, I, A, P |
| Epilepsy detector | software/hardware error | I, A |
| Health Guide | Malware and vulnerability exploit side-channel attack | C, I, A, PC, P |
| Heart rate monitor | wireless attack | C, I, A, P |

Column 1 corresponds to PHSs and medical devices. Column 2 corresponds to the threat types they are prone to. Column 3 corresponds to the risks associated with each system with respect to the particular threat. Confidentiality, integrity, availability, and privacy risks are referred to C, I, A, and P, respectively.

Safety Solutions

Close-range Communication

Limiting the communication range is a simple and intuitive way of limiting wireless attacks. A radio frequency identification (RFID)-based channel between medical devices and external controllers is often proposed in this context. However, an attacker with a strong enough transmitter and a high-gain antenna can attack the wireless channel even if the channel is for RFID-based communication. For an RFID channel, the attacker can access the IWMD from up to ten meters away.

An alternative approach includes near-field communication (NFC), an extension to RFID, which is gaining increasing attention, especially due to its integration on mobile phones. The typical working distance for NFC is up to twenty centimeters. However, there is no guarantee that an attacker with a high-gain antenna cannot read the signal from outside the intended range, e.g., one meter away.

Another approach that can help limit the communication range is body-coupled communication (BCC). In contrast to conventional wireless communication, BCC uses the human body as the transmission medium. The communication range is limited to the proximity of the human body. Experimental results in show a promising attenuation in signal strength measured from some distance when comparing the BCC channel signal to the air channel signal.

In addition to communications that are designed to be inherently short-range, measures can be taken to enforce close range communication. An access control scheme based on ultrasonic distance-bounding is possible. In this scheme, an IWMD grants access to its resources to those devices that are close enough. Shielding is another way of enforcing close range communication. A metal shield that restrains wireless signals from traveling beyond it can effectively eliminate radio eavesdropping attackers at a distance.

However, limiting the communication range is effective against wireless attacks launched beyond a certain distance. An attacker may approach within a small distance of the patient and even make physical contact without raising suspicion (e.g., in a crowded subway station). Therefore, even close-range communication schemes cannot defend against substantially all close-range attacks.

Cryptography

Cryptography is one approach for securing the wireless communication channel and preventing unauthorized access. It can protect device integrity as well as data confidentiality. However, conventional cryptographic methods, such as symmetric- and asymmetric-key cryptography, are not directly applicable as the problem of distributing keys to legitimate parties remains a hindrance. For example, encryption prevents medical professionals from accessing the patient's health data in emergency situations. As a possible solution, a universal key may be preloaded in devices of the same model that the ambulance staff can request from the manufacturer or patient's doctor in emergencies. However, this scheme is inherently unsafe as attackers can discover the secret key of a particular model through side-channel attacks or by hacking into the doctor's computer.

Another straightforward key-distribution solution is to ask patients to carry cards or bracelets imprinted with the secret keys of their devices. To prevent the imprints from being lost or damaged, the keys could be printed into the patient's skin using ultraviolet-ink micropigmentation. These "tattoos" become visible under ultraviolet light, which is how the ambulance staff can find the keys and access the devices. To some extent, this approach protects the patient from close range attacks as well, since although the attacker may be in close proximity, it is unlikely that the attacker can lift up the patient's sleeves while shining ultraviolet light without raising suspicion.

IMDGuardian is a cryptographic scheme for implantable cardiac devices. It utilizes the patient's electrocardiography signals for key extraction so that no pre-distributed secrets may be needed and rekeying is easy. However, attackers may be able to extract the key through physical contact with the patient.

Cryptographic methods cannot defend IWMDs against denial-of-service attacks that repeatedly request communication with the IWMD. The IWMD's battery is depleted in verifying the incoming requests.

External Device

To preserve IWMD battery power, the verification of incoming requests can be offloaded to a trusted external device. One such device, called Communication Cloaker. The Cloaker mediates communications between the IWMD and pre-authorized parties, and causes the IWMD to ignore incoming communications from unauthorized programmers. Cloakers are wearable. If the Cloaker is missing or broken, the IWMD accepts and responds to incoming communications. Therefore, in emergency situations, the medical staff can remove the Cloaker in order to access the IWMD. Since the burden of computation is offloaded to the external device, this approach can protect the IWMD against battery-draining attacks. Unlike IWMDs, the external device can be easily recharged.

Another external device, a personal base station called the "Shield." The shield works as a relay between the IWMD and external programmer. It is designed to receive and jam the IWMD messages at the same time, so that others cannot decode them. It then encrypts the IWMD message and sends it to the legitimate programmer. The shield also protects the IWMD from unauthorized incoming commands by jamming all the messages sent directly to the IWMD. Commands should be encrypted and sent to the shield first. The shield then sends legitimate commands to the IWMD. Therefore, the shield does not require any change in commercial IWMDs, but requires changes in all programmers. Since the messages from the IWMD are jammed and the communication between the programmer and the shield is encrypted, the confidentiality of IWMD messages is protected. However, when the shield sends programmer's commands to the IWMD, the commands are not encrypted, and the confidentiality of the commands is not protected.

Fault-tolerant Design

Complex electronic circuits are used in life-helpful health-care systems, where reliability is of importance. Though manufacturing-time test in some embodiments identifies a large number of circuit defects, exhaustive testing and attaining complete fault coverage may not be feasible. Hardware failures, including undetected manufacturing defects, wear-out faults and transient faults, pose a threat to the reliable operation of the circuit. By concurrent detection, diagnosis and correction of fault effects, fault-tolerant designs allow a system to continue operating properly in the event of faults in its components. Fault tolerance can also be extended to cope with software errors caused by design inadequacies.

In general, fault tolerance requires some form of redundancy, either in time, hardware, or information. Hence, it incurs either performance degradation or hardware overhead. For example, triple modular redundancy, a well-known fault tolerance scheme that employs three copies of a module and uses a majority voter to determine the final output, comes with more than three times the cost of the original circuit. Despite their high cost, fault-tolerant design techniques may be warranted in safety-helpful medical devices and PHSs.

Software Verification

Currently, there are no widely accepted techniques in use for the development or the verification of software in medical devices. The FDA's assessment of device software only concentrates on development processes, not the integrity of the software itself. Such an approach, though not entirely without aspects, depends mainly on crafted test case construction and the results of test case execution for validation, with little regard to the properties of the actual code. It has been argued that perhaps using open-source software is more secure and reliable for medical applications, as it enables continuous and broad peer-review that identifies and eliminates software errors.

Formal methods have been suggested as a means to design and develop reliable medical systems. Formal methods are mathematical techniques for the specification, development and verification of software and hardware systems. The specifications used in formal methods are well formed statements in a mathematical logic, and formal verification includes rigorous deductions in that logic. Therefore, formal methods provide a means to symbolically examine the state space of a system and establish a correctness or safety property that is true for possible inputs. For medical systems, however, correctness is an important attribute as undetected errors in components may cause harm.

Secure Execution Environment

While PHSs are subject to unique threat models and attacks, as described in previous subsections, software attacks will continue to be a commonly utilized approach for compromising their security, due to the relative ease and low cost of launching such attacks. In this context, the "weakest link" of a PHS, i.e., the component that exposes the largest attack surface and is accessible to software attacks, is the health hub (smartphone or PDA), which executes the medical applications (for logging of health data, display of data to the user, and communication with remote medical professionals and health information services). On the other hand, as reflected by the rapid proliferation of "application" marketplaces for mobile devices, users are likely to use their smartphones or PDAs to execute several untrusted and potentially vulnerable applications as well. In the extreme case, the operating system on the hub may itself be compromised, making it trivial to subvert the medical applications that execute under its full control. Thus, it becomes helpful to provide a secure execution environment for the medical applications in the face of other untrusted applications and also an untrusted operating system (OS).

While it may not be feasible to secure applications from a compromised OS, it is possible to achieve a secure execution environment that provides isolation for selected, security-helpful applications. The isolation may be based on physical separation (e.g., IBM's secure co-processor) or logical separation, in which both the sensitive and untrusted code are run on the same processor, but are isolated either using an additional layer of software, such as virtualization, or through additional hardware support (e.g., Intel TXT and ARM TrustZone).

A secure architecture can be adopted to build a secure run-time environment for medical applications. The two key technologies used are secure virtualization and trusted computing.

For PHSs, virtualization is a promising technology that can be utilized to enhance security by providing isolated execution environments for different applications that require different levels of security. The medical applications are all protected in a separate virtual machine (VM), which is referred to as the medical VM. The medical VM is a restricted environment in which only medical applications and the supporting software libraries are executed, isolated from the other applications running on the system.

Trusted computing is a set of standards that is widely gaining popularity in general-purpose computing systems. Trusted computing may require a "root of trust" in the system for tamper-proof storage and attestation, which in some embodiments is realized by adding a separate tamper-proof hardware component called the Trusted Platform Module (TPM) to the system. In size-constrained and resource-constrained platforms, such as smartphones and PDAs, which is used as the health hub, it is currently not common to see hardware TPMs. In such cases, the use of a software TPM based on software emulation of TPM functions within an isolated execution environment has been demonstrated.

Table II summarizes some of the above-mentioned solutions along with the types of threats that each solution can defend against. Column 1 refers to the defense techniques. Column 2 corresponds to the threat that each solution can defend against. Columns 3-6 provide the security evaluation for each defense solution against the corresponding threat.

TABLE II

SECURITY EVALUATION OF DEFENSE SOLUTIONS

| Defense | Threat | Confidentiality | Integrity | Availability | Privacy |
|---|---|---|---|---|---|
| RFID-based communication, NFC, BCC, access control based on distance | long-range wireless attack | Y | Y | N | N |
| Cryptography | wireless attack | Y | Y | N | N |
| "Cloaker" | wireless attack | Y | N | N | N |
| "Shield" | wireless attack | Y | Y | N | Y |
| Formal verification | software/hardware error | Y | Y | Y | n/a |
| Fault-tolerant design | software/hardware error | Y | Y | Y | n/a |
| Secure execution environment | malware and vulnerability exploit | Y | Y | Y | Y |

FIG. 1 is a block diagram of a system 10 including a medical device security monitor (MedMon) 20. The system includes a first medical device 30 that is associated with a patient, e.g., the device may be implanted within or worn by the patient a patient. The first medical device 30 generally includes a communication interface 32. The system also includes a second device 40 that generally includes a communication interface 42. The second device 42 may be an external programmer or other device configured for communication with the first medical device 30. The MedMon 20 is also configured with a communication interface 22. Wireless communications between the MedMon 20, first medical device 30 and second device 40 is generally shown by dashed lines 50. It should be understood that a wide variety of wireless communications techniques may be used without departing from the scope of this disclosure including the approaches discussed above such as Bluetooth (e.g., IEEE 802.15), Zigbee (e.g., IEEE 802.15.4), WiFi (e.g., IEEE 802.11), near field communication (e.g., ISO/IEC 14443) and the like. In operation, the MedMon 20 snoops on all communications between the first medical device 30 and the second device 40 and analyzes said communications for compliance to a set of security policies.

Figure 2:
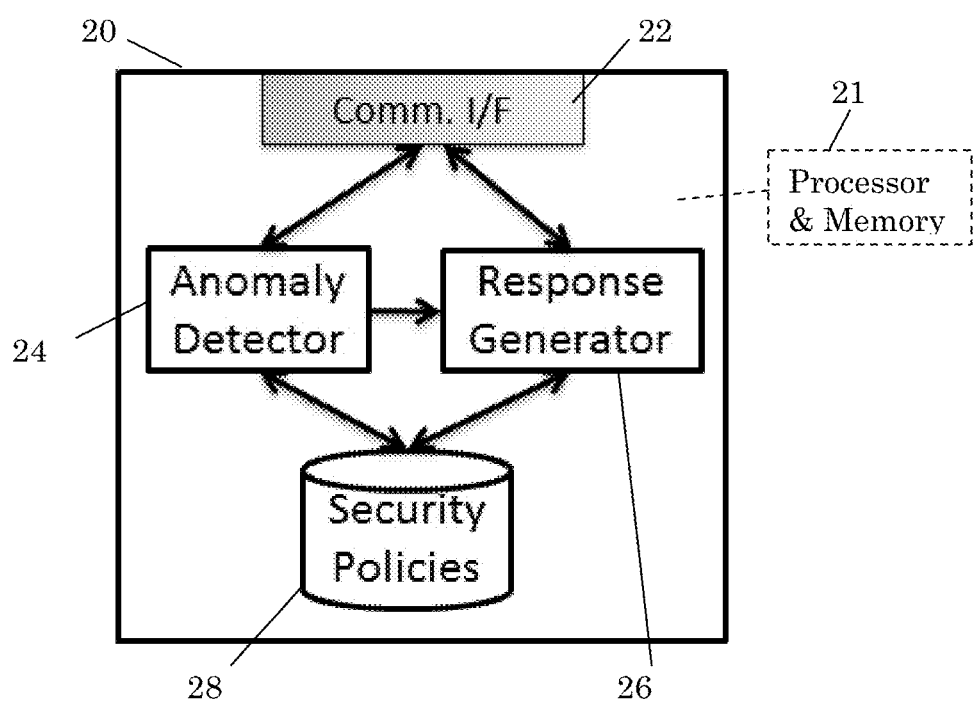
FIG. 2 is a block diagram of the MedMon.

FIG. 2 is a block diagram of a MedMon 20 including a communication interface 22, an anomaly detector 24, response generator 26, and security policies 28. It should be understood that the MedMon 20 will generally be implemented on a device that includes a processor and memory as generally shown by block 21. The communication interface 22 snoops on the communications to/from the medical device (e.g., 30 in FIG. 1). The anomaly detector 24 analyzes the communications with respect to the security policies and notifies the response generator once an anomaly is detected. The response generator produces a suitable response, e.g., generating a warning message for the user or generating a jamming signal through the communication interface such that the anomalous communication to the medical device is disrupted.

FIG. 3 is block diagram showing a generic architecture of a personal healthcare system (PHS) 100. The 100 generally includes one or more medical devices 120a-120c associated with a patient, e.g., the devices may be implanted within or worn by the patient a patient. The system 100 also includes a second device 130. In this example, the second device 130 is implemented in the patient's smartphone and is generally configured for wireless communications with the medical devices 120a-120c. In general the medical devices 120a-120c and the second device form part of the patient's body area network (BAN). The second device 130 is coupled to a health server 140 via traditional communications, e.g., digital cellular communication as shown by reference number. In general, the health server may be configured to activity in connection with the patient's medical devices. The health server may also function as a programming device and provide scheduling and programming information for the patient's medical devices. The second device 130 and health server may also communicate with other medical devices such as a third medical device 160 (in this example a doctor's smartphone).

In the disclosed defense framework, security is delivered by the MedMon. The MedMon may be a wearable external device added to the BAN of a PHS. To accommodate different devices and patient needs, the MedMon may be trained and configured first in order to learn the characteristics of normal behavior. For both training and actual use, it must be placed at a fixed position relative to the IWMD. When in use, the MedMon quietly monitors communications among the different components of a PHS. It searches for anomalies in transmitted signals to determine whether a wireless attack is being launched against the PHS.

Figure 4A:
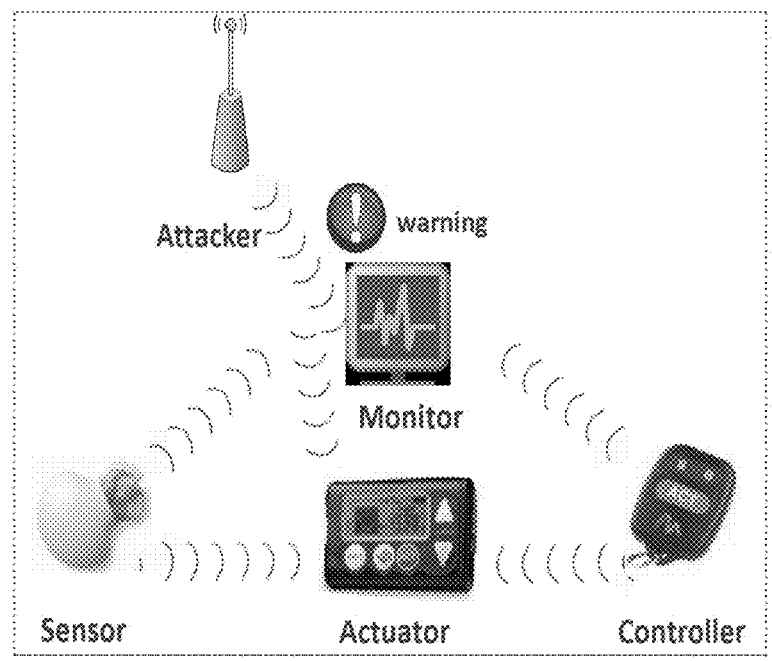
FIG. 4a is a block diagram showing a passive mode configuration where: once an attack is identified the MedMon is configured to provide a warning to the patient.
Figure 4B:
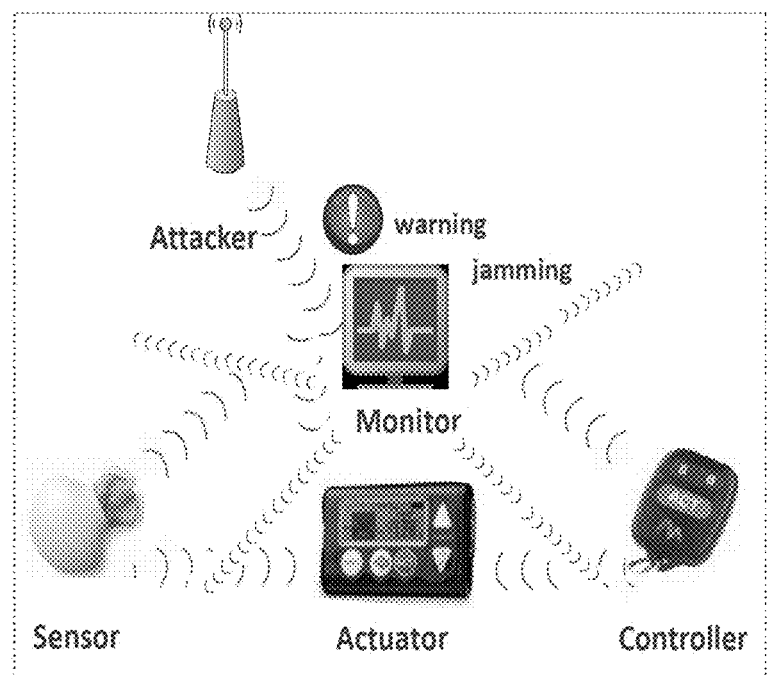
FIG. 4b is a block diagram showing an active mode configuration where: once an attack is identified the MedMon is configured to jam communications.

When anomalies are identified, indicating a possible attack, the MedMon can respond passively or actively, depending on its configuration for this type of anomaly or attack. FIG. 4a is a block diagram showing a passive mode configuration where: once an attack is identified the MedMon is configured to provide a warning to the patient. FIG. 4b is a block diagram showing an active mode configuration where: once an attack is identified the MedMon is configured to jam communications.

The MedMon may be set to the passive (active) mode for a particular anomaly if the potential damage is low (high). In the passive mode, it provides a warning to the patient e.g., through an alarm or vibration, without interfering with ongoing communication. In the active mode, in addition to alerting the patient, it interferes with the transmission by sending jamming signals, so that the suspicious transmission is blocked before it can complete and succeed in altering the state of the devices.

MedMon's active response of jamming and use of an external device is somewhat similar to the design of the Shield (see, S. Gollakota, H. Hassanieh, B. Ransford, D. Katabi, and K. Fu, "They can hear your heartbeats: Non-invasive security for implantable medical devices," in Proc. ACM Conf. Special Interest Group on Data Communication, August 2011). However, unlike the Shield, the MedMon passively monitors the communication and only interferes when an anomaly is detected. Although the shield may work well for PHSs consisting of an IWMD and an external programmer, it is not suitable for PHSs in which IWMDs communicate with each other, because changes must be made to any device that needs to communicate with the IWMD under protection. On the contrary, the MedMon does not require any change in existing communication protocols and therefore requires no change in other devices in the PHS.

Anomaly Detection

Anomaly detection techniques are commonly used in diverse domains, but have not been explored in the context of medical devices. In one scenario, the MedMon infers the legitimacy of a packet using a sequence of checks. Transmission is allowed only if it passes these checks. The potential anomalies may be classified into two categories: physical and behavioral, as discussed next.

Physical Anomalies

The MedMon starts its examination by observing the physical characteristics of the transmitted signal. Such characteristics may include the received signal strength indicator (RSSI), time of arrival (TOA), differential time of arrival (DTOA), and angle of arrival (AOA), all of which are well-known indicators from the area of radio location. In radiolocation, RSSI, TOA, and DTOA are used to estimate the distance of a transmitter from the receiver, and AOA is used to determine the transmitter's direction in relation to the receiver. Knowing these characteristics of the transmitter will allow the MedMon to verify its legitimacy with high confidence. However, the relative positions of the PHS components and the MedMon may not always stay the same. For example, the patient may hold the remote control at different angles relative to the MedMon. Fortunately, the MedMon does not have to precisely locate the transmitting device used in the attack. For legitimate transmitting devices in the PHS, some of the above-mentioned metrics have relatively steady values. Thus, thresholds can be used to demarcate boundaries between normal and abnormal values, as discussed below.

RSSI: If the distance between the MedMon and each transmitting device is known and expected to remain relatively constant, the signal strength from the device can be expected to fall within a specific range. An anomaly is detected if the signal allegedly sent by the device has unusually high or low strength.

TOA: If a transmission is scheduled to occur at specific points in time, the occurrence of the transmission at a non-scheduled time reveals an anomaly.

DTOA: If a transmission is scheduled to occur periodically at certain time intervals, early arrival of the transmission signal is recognized as an anomaly.

AOA: Assuming the MedMon is carried at a fixed location on the patient, e.g., attached to the right side of the patient's belt, a transmitting device, e.g., a sensor on the patient's back, will have a fixed angle relative to MedMon. In such cases, AOA could be used to examine whether the signal is arriving from the correct direction. For example, the MedMon will report an anomaly if it receives sensor signals from the front, when it expects them to come from the back.

Behavioral Anomalies

An examination of physical indicators cannot guarantee all attacks will be caught. For example, attack signals might have the physical characteristics that satisfy all requirements by chance or through sophisticated design. However, although an attack signal may be physically indistinguishable from a normal signal, the underlying information (commands or data) can typically be distinguished due to its intention to cause harm to the patient, e.g., a malicious command that orders repeated or large-dose drug injections, or forged data that feign sudden changes in vital signs to induce unnecessary drug delivery.

Anomalies in the underlying information are considered to be behavioral anomalies. The MedMon keeps a record of the historical data and commands. Such information may be stored in MedMon memory, e.g., processor/memory 21 in FIG. 2. When new command/data arrive, the MedMon compares them to the historical record to decide whether the new command/data constitute a behavioral anomaly.

When a command anomaly is detected, such as for repeated drug injections, the MedMon may prevent the new command from being executed by jamming the command signal, in order to protect patient health and safety. If the command is authorized by the patient, the patient can simply revise the command or change the anomaly definition in the MedMon's configuration.

It should be understood that behavioral anomaly detection may not require storage of historical information. Comparing to historical data is one way of accomplishing behavioral anomaly detection, but other approaches are possible. For example, legal value ranges for some fields of a communicated message may be programmed into MedMon, which simply compares each snooped communication with the value ranges, without any historical information. When a data anomaly is detected, such as a sudden change in the patient's vital signs, the MedMon generates a warning. Abnormal data may be generated by an attacker or may actually represent a deteriorating patient condition. In either case, the MedMon's warning alerts the patient to an attack or a health condition that he/she should be concerned about.

The firmware on some devices may provide functionality similar to that of behavioral checking, which verifies whether measured values are within bounds and raises an alarm if they are not. However, not all device firmware does so. For devices on which such a functionality or parameter reconfigurability is absent, firmware updates may require device recalls and may be limited by the capacity of existing hardware. The MedMon provides behavioral checking without requiring any changes to the IWMDs. If the firmware already provides the same protection, behavioral checking can be turned off on the MedMon.

Protection Layers

Figure 5:
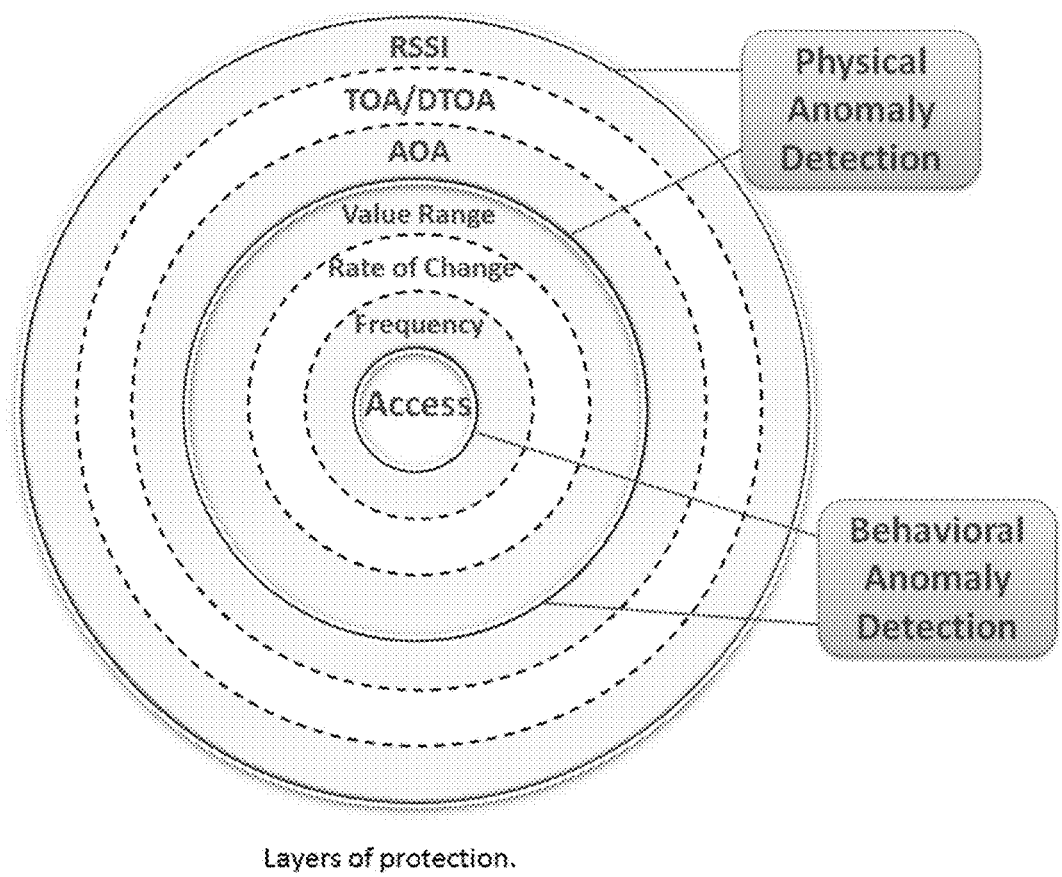
FIG. 5 is a block diagram showing protection layers.

The examination process is analogous to peeling off the layers of an onion. We refer to these layers as protection layers. FIG. 5 is a block diagram showing protection layers. The outer layers, i.e., the physical indicators, are examined first. If the transmitted signal passes the examination in the outer layers, the MedMon searches for data or command anomalies in the signal's underlying content. If no anomaly is found, the signal is deemed to be safe and granted access to the target device. A general description of the anomaly detection process is discussed below in connection with FIGS. 11 and 12 below.

An implicit assumption in the above scenario is that the signal under examination is transmitted or allegedly transmitted from a registered device (the device PIN is known to other devices in the PHS and to the MedMon). If the transmitted signal carries a PIN from an unregistered device, e.g., the controller of another patient nearby, the MedMon does not need to perform any examination of the signal, since the signal will be ignored by IWMDs in the PHS anyway. Needless to say, it should not try to jam communications in a nearby patient's BAN. Therefore, the MedMon first examines the PIN carried by the transmitted signal before taking any further action.

Security Policies

Anomalies can be defined within security policies. Security policies define what the MedMon's response should be to each detected anomaly. Each transmitting device has its own set of security policies. The MedMon is guided by the security policies of the transmitting device when snooping on its transmission.

Table III shows examples of security policies that could be used. These policies may be different for different PHSs. The parameters mentioned in Table III can be set to predefined values or else tailored to the patient's condition and environment. Values of parameters associated with physical anomalies, e.g., $A_h$ and $\Delta t_h$, can be generated automatically at the end of a training period. Values of parameters associated with behavioral anomalies, e.g., $D_{th}$ and $r_{th}$, can be selected based on the advice of the doctor.

TABLE III

EXAMPLES OF SECURITY POLICIES

| Type | Anomaly | Response |
| --- | --- | --- |
| Physical | RSSI is greater than $A_h$ or smaller than $A_l$ | Raise warning, jam |
| | TOA does not fall in any of the time ranges ($t_l$ (m), $t_h$ (m)) | Raise warning, jam |
| | DTOA is greater than $\Delta t_h$ or smaller than $\Delta t_l$ | Raise warning, jam |
| | AOA is greater than $\alpha_h$ or smaller than $\alpha_l$ | Raise warning, jam |
| Behavioral | Data value is greater than $D_h$ or smaller than $D_l$ | Raise warning |
| | Rate of change of data value is greater than $r_{th}$ or smaller than $-r_{th}$ | Raise warning |
| | Injection dose is larger than $D_{th}$ | Raise warning, jam |
| | Repeated n injections in the past $\Delta T$ | Raise warning, jam |
| | Total injected dose greater than $V_{th}$ in the past $\Delta T$ | Raise warning, jam |

During the training period, the patient carries the MedMon with the PHS operating normally. After collecting a sufficient number of values for RSSI, TOA, DTOA, and AOA for each transmitting device, the MedMon determines if each parameter has values that fall in a certain range and, if so, decides the thresholds for the parameter. If a parameter does not have a range of normal values, it is not included in the device's security policies. As explained above, such information may be stored in MedMon memory, e.g., processor/memory 21 in FIG. 2.

Note that policies related to TOA and DTOA are only helpful if data transmissions occur periodically or at specific points in time. Fortunately, irregular transmissions are most likely initiated by the patient. The MedMon can therefore apply strict policies to jam or raise a warning by default, as discussed below. Sometimes, even if data transmissions are scheduled to occur periodically or at specific times, the actual occurrence may not exactly be in accordance with the schedule, because the communication protocol may require verifying the absence of other traffic before transmission, or retransmissions are performed after failed transmissions. In such cases, TOA and DTOA, with wider acceptable ranges, may still be quite useful, especially if the transmissions occur fairly infrequently (e.g., a few times a day) and the delay till successful transmission is relatively small (e.g., several minutes).

Figure 11:
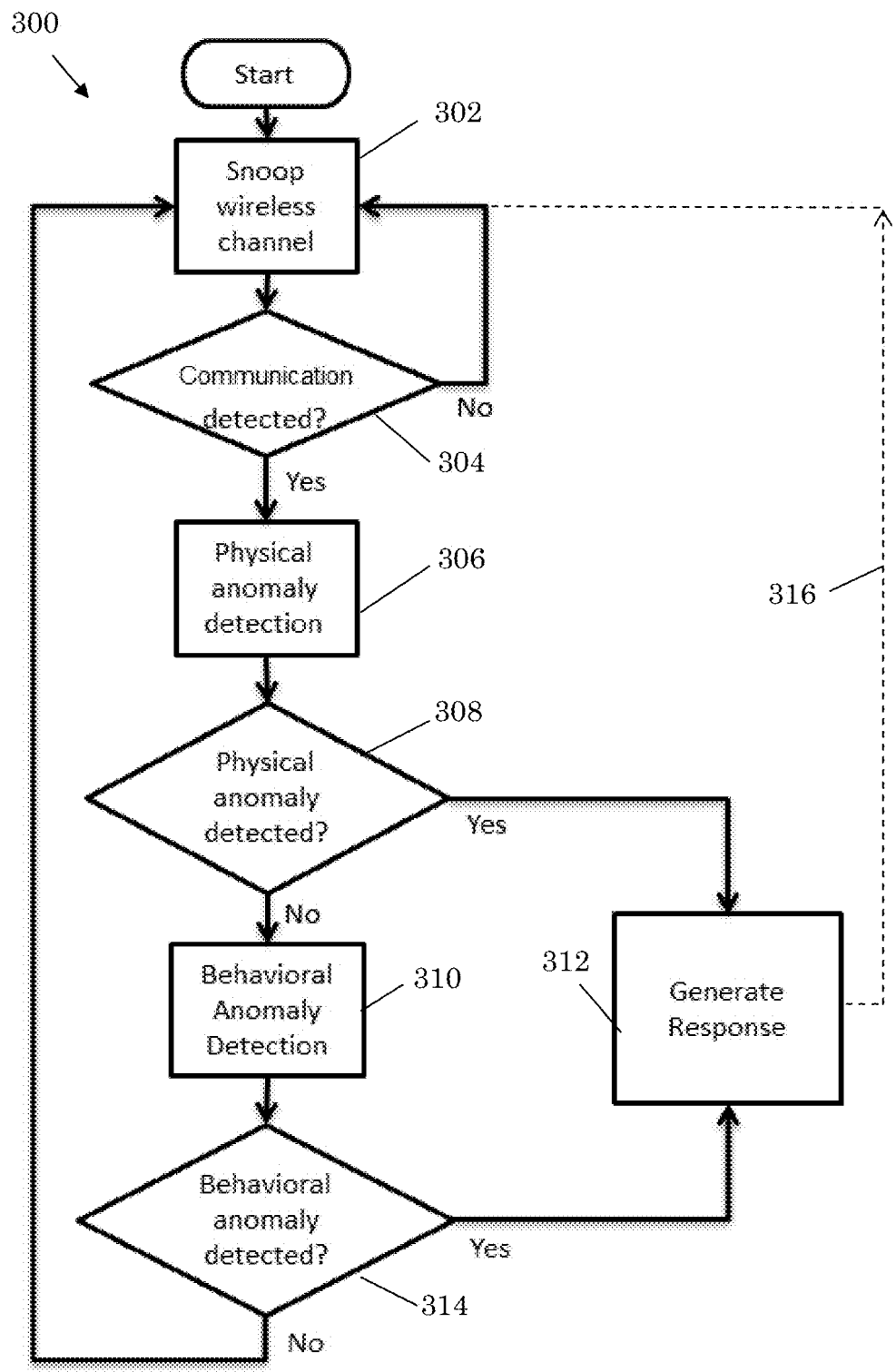
FIG. 11 is a flow chart showing a generalized anomaly detection process.

FIG. 11 is a flow chart showing a generalized anomaly detection process 300. It should be understood that any flowcharts contained herein are illustrative only and that other entry and exit points, time out functions, error checking routines and the like (not shown) would normally be implemented in typical system hardware/software. It is also understood that system hardware/software may run continuously after being launched. Accordingly, any beginning and ending points are intended to indicate logical beginning and ending points of a portion of code or hardware function that can be integrated with other hardware or portions of code and executed as needed. The order of execution of any of the blocks may also be varied without departing from the scope of this disclosure. Implementation of these aspects in hardware and/or software is readily apparent and well within the grasp of those skilled in the art based on the disclosure herein.

The MedMon snoops on the communications between the medical devices of interest, e.g., a first medical device and a second device such as an insulin pump and a remote control as shown by block 302 and 304. Once communications are detected, the communication is tested for a physical anomaly as shown by block 306. If a physical anomaly is detected, a response is generated as shown by block 312. If no physical anomaly is detected, the communications are examined for a behavioral anomaly as shown by block 310. If a behavioral anomaly is detected, a response is generated as shown by block 312. If no physical anomaly is detected, the process is repeated for subsequent communications. It should be understood that once a response is generated the user may need to intervene. Ultimately, the process will resume again at block 302 as shown by dashed line 316.

Figure 12:
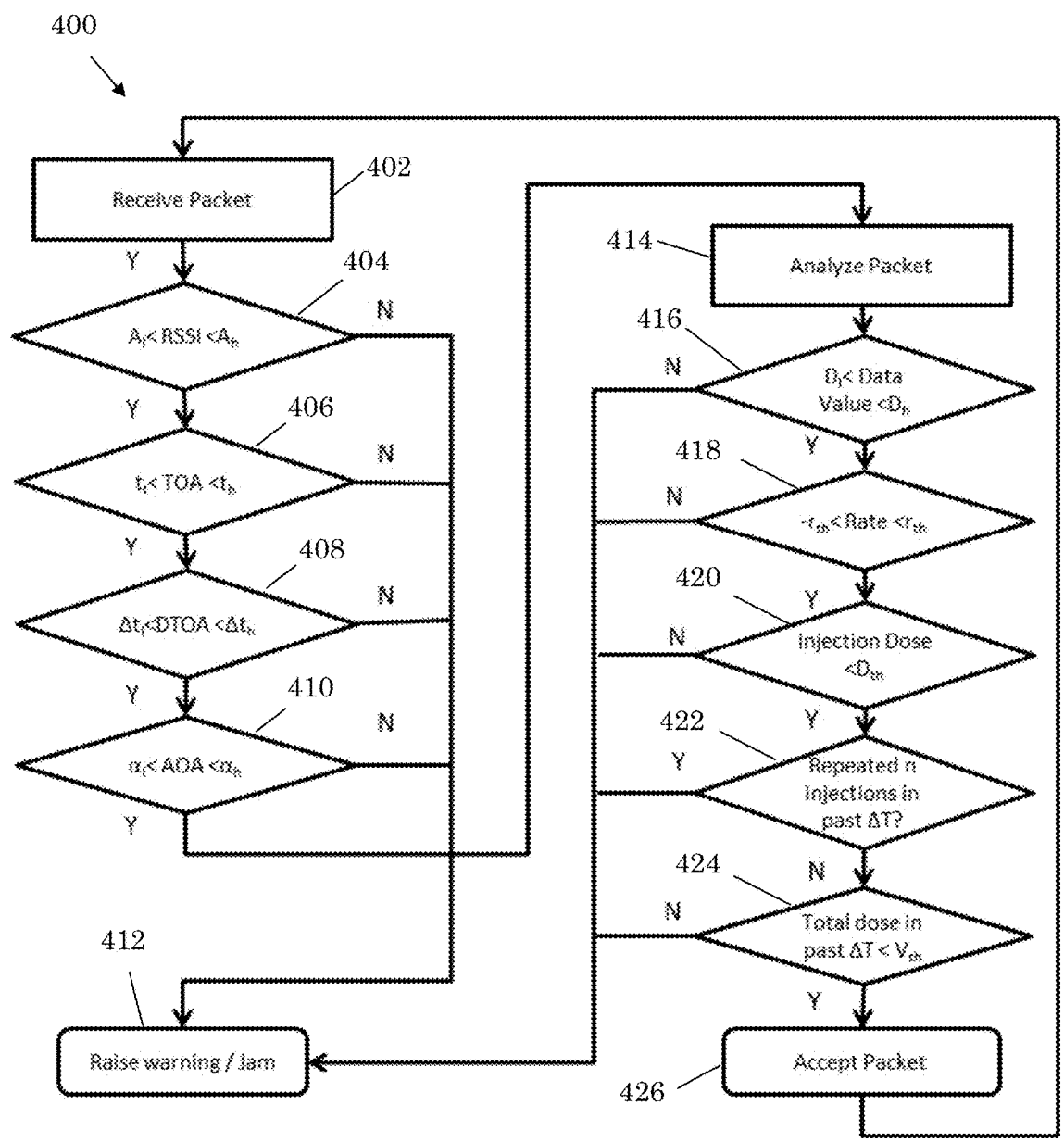
FIG. 12 is a flow chart showing a more detailed implementation of an anomaly detection process.

FIG. 12 is a flow chart showing a more detailed implementation of an anomaly detection process 400. The MedMon snoops on the communications between the medical devices of interest by receiving a packet transmitted by one of the medical devices as shown by block 402. The packet is then tested for a variety of physical anomalies as shown by blocks 404-410. If an anomaly is detected then a response is generated as shown by block 412. Otherwise, the packet is analyzed for behavioral anomalies as shown by block 414. A physical anomaly is detected if the RSSI of the packet falls outside of a range defined by $A_l$ and $A_h$ as shown by block 404. A physical anomaly is also detected if the TOA of the packet falls outside of a range defined by $t_l$ and $t_h$ as shown by block 406. A physical anomaly is also detected if the DTOA of the packet falls outside of a range defined by $\Delta t_l$ and $\Delta t_h$ as shown by block 408. A physical anomaly is also detected if the AOA of the packet falls outside of a range defined by $\alpha_l$ and $\alpha_h$ as shown by block 410. It should be understood that all physical anomaly parameters $A_l$, $A_h$, $t_l$, $t_h$, $\Delta t_l$, $\Delta t_h$, $\alpha_l$ and $\alpha_h$ may be stored in MedMon memory, e.g., processor/memory 21 in FIG. 2. Such parameters may be initialized and updated as is well known in the art.

If no physical anomaly is detected the packet is then tested for a variety of behavioral anomalies as shown by blocks 416-424. If an anomaly is detected then a response is generated as shown by block 412. For example, a behavioral anomaly is detected if the packet data value falls outside of a range defined by $D_l$ and $D_h$ as shown by block 416. A behavioral anomaly is also detected if the rate of change of the data value falls outside of a range defined by $-r_{th}$ and $r_{th}$ as shown by block 418. For systems having an injection delivery device, a behavioral anomaly is also detected if the injection dose falls exceeds $D_{th}$ as shown by block 420. A behavioral anomaly is also detected if n repeated injection commands are received in a time range specific by $\Delta t$ as shown by block 422. A behavioral anomaly is also detected if the total dose in the time range specific by $\Delta t$ exceeds $V_{th}$ as shown by block 424. Otherwise no anomaly is detected (the packet is considered acceptable) and the process continues again with block 402. It should be understood that all behavioral anomaly parameters $D_l$, $D_h$, $-r_{th}$, $r_{th}$, $D_{th}$, n and $\Delta t$ may be stored in MedMon memory, e.g., processor/memory 21 in FIG. 2. As explained above, such parameters may be initialized and updated as is well known in the art.

Implementation and Evaluation

It should be understood that the MedMon may be used with a wide variety of medical devices. The following is a description of a prototype implementation of MedMon for a glucose monitoring and insulin delivery system.

Example Setup—Glucose Monitoring/Insulin Delivery

Glucose monitoring and insulin delivery systems are used for the treatment and management of diabetes. They commonly employ wireless communication among system components to form a real-time monitoring and response loop. Additional disclosure pertaining to glucose monitoring/insulin delivery systems may be found in: Chunxiao Li, Raghunathan, A., Jha, N. K., Hijacking an insulin pump: Security attacks and defenses for a diabetes therapy system, e-Health Networking Applications and Services (Healthcom), 2011 13th IEEE International Conference, p 150-156, June 2011, which is incorporated herein in its entirety. In this example, the system includes the following components:

A glucose sensor, which samples blood glucose levels on a continuous basis, typically every few minutes.

A manual glucose meter, which is used to manually measure blood glucose levels.

An insulin pump, which performs autonomous administration of insulin through subcutaneous infusion.

A remote control, which is used to program the insulin pump to reconfigure parameters or to cause the pump to inject a bolus dose (e.g., in advance of an event that will cause a surge in blood glucose levels, such as a meal).

Figure 6A:
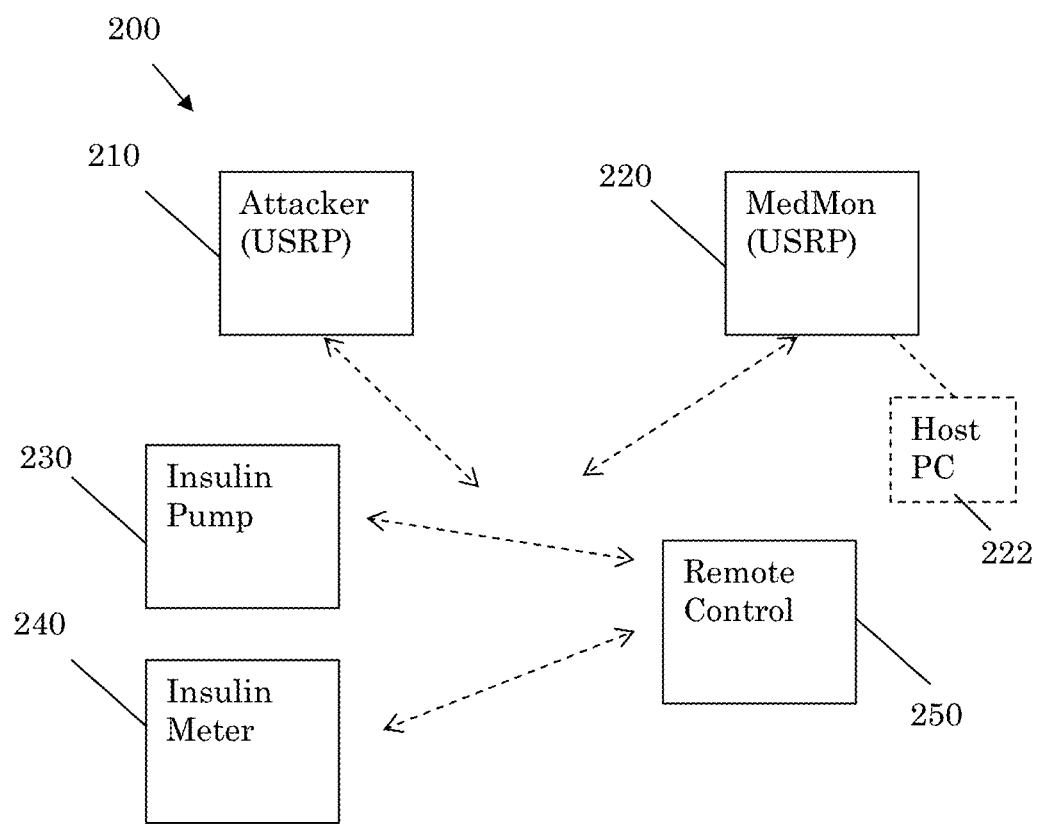
FIG. 6a is an example glucose monitoring/insulin deliver setup including a glucose meter, insulin pump, remote control, an attacker and a MedMon.

The example setup, as shown in FIG. 6a, includes a manual glucose meter 240, insulin pump 230, remote control 250, an attacker 210 and the MedMon 220. The attacker 210 and MedMon are at least partially implemented using Universal Software Radio Peripheral (USRP) boards, e.g., available from Ettus Research, http://www.ettus.com. The USRP is an off-the-shelf software radio platform. It can intercept radio communications within a frequency band and generate wireless signals with different frequency, modulation, and power configurations.

Each USRP has two transmit/receive paths that can be used independently. To perform attacks, one path of the attacker USRP is used for eavesdropping and the other path for transmitting attack signals. The MedMon can be implemented in passive mode using only one path of the USRP configured as a receiver. Implementation of the MedMon active mode requires both paths, where one path acts as a receiver and the other as a transmitter to send jamming signals. On the USRP that emulates MedMon 220, the sampled RF signal is down-converted to the baseband and then sampled at 64 MS/s. The samples are then decimated to 320 kS/s before being transferred to the computer via USB in the form of a stream of floats. Note that, in this example, the MedMon 220 functionality is implemented in part on the USRP board, while the rest of it is implemented in the GNU Radio software framework that is run on a host PC 222. In this configuration the data transfer over USB has a latency of around 1 ms. However, an integrated MedMon implementation will not have this latency.

Figure 6B:
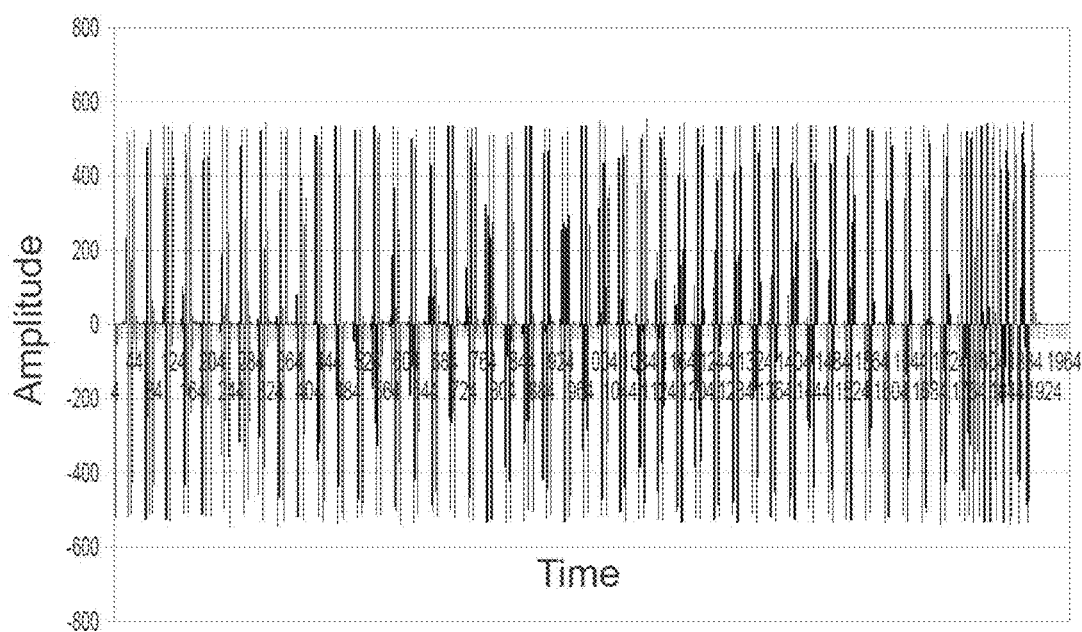

In this example, it was possible fully reverse-engineer the communication protocol of the remote control and use the USRP to act as an attacker and launch attacks. The intercepted and down-converted wireless signal sent by the remote control 250 is shown in FIG. 6b. A data packet contains a synchronizing sequence of "0"s and "1"s, device type, device PIN, command, cyclic redundancy check (CRC) bits, etc.

Attack Scenarios

The scope of potential attacks on the insulin delivery system can be categorized based on the wireless links being exploited and the nature of the security breach.

Classification Based on Exploited Links

In the insulin delivery system, there exist several wireless links: the link from the sensor to the pump to continuously transmit glucose data, the link from the manual meter to the pump to transmit glucose data (the messages on this link are manually triggered), and the link from the remote control to the pump to transmit control commands. All three links can be exploited by an attacker.

Classification Based on Security Breaches

By exploiting a particular wireless link, the following attacks can be launched. If the attacker does not know the device PIN of the remote control or glucose meter/sensor, some of the possible attacks are:

Privacy attacks: Eavesdropping on any wireless link in the insulin delivery system exposes: (1) the existence of the therapy and the glucose level, and thus the medical condition of the patient, (2) the device type, and (3) the device PIN, which gives the attacker an open door to launch all the attacks discussed in the next group.

Integrity attacks: Even without the knowledge of the device PIN, by relaying transmission signals (intercepting and replaying later), the attacker can still control the insulin pump or report an incorrect (past) glucose reading to the insulin pump.

Availability attacks: Attackers can simply jam the communication channel, causing incorrect operation.

If the attacker knows the device PIN of the remote control, manual glucose meter or glucose sensor, either by reading the printed device PIN from the medical device or through eavesdropping, attacks can be launched by impersonating the respective device. The consequences of such attacks could include: (1) the attacker can stop insulin injection into the human body, (2) the attacker can resume insulin injection into the human body if it is currently stopped, and (3) the attacker can inject a bolus dose into the human body, which may lead to hypoglycemia and, hence, endanger the patient's life.

Design of Security Policies

The signals transmitted from the manual glucose meter and the remote control are initiated by the patient. Commands allegedly sent by the remote control or data allegedly sent by the manual glucose meter, which are not authorized by the patient, must have been sent by an attacker. Based on this observation, it is possible to adopt the strictest policy for remote control and manual glucose meter data transmissions: the MedMon jams any command signal by default and raises a warning for any meter or remote control data transmission by default. This is equivalent to defining all remote control and meter data packets as behavioral anomalies. By doing so, we ensure that fake commands sent by the attacker do not go through.

However, commands sent by the patient are jammed too (false positives), rendering the glucose meter and remote control unusable. Fortunately, this problem can be easily resolved at the cost of a slight increase in patient effort. The patient can simply disable jamming or turn off the MedMon before initiating transmission from the manual glucose meter or remote control to allow the command to pass to the pump. The patient can enable jamming or turn on the MedMon right after the transmission is completed. This slight inconvenience is in exchange for much greater confidence in preventing attack commands from harming the patient. In case the attacker continuously transmits forged messages, the patient should not turn the MedMon off while "prolonged" warnings are reported. In addition, continuous malicious signals can interfere with normal signals. If the insulin pump does not respond to normal commands due to interference, the patient should immediately turn the MedMon back on in case the interference is caused by an attack signal.

The MedMon raises warnings when data transmissions from the manual glucose meter or remote control are detected. The patient should expect to receive warnings when sending data from these devices to the insulin pump. If a warning for meter data transmission arrives when the patient is not using the glucose meter, the patient knows that an attack is taking place. Furthermore, the warnings issued by the MedMon also ensure that a patient does not inadvertently forget to turn off jamming before transmitting a legitimate command. Finally, the small window of vulnerability, when the MedMon is disabled, can be eliminated by having the MedMon operate in the passive mode and merely report successful data transmissions to the user. If the user sees more transmissions reported than he/she generated, evasive action may be taken, such as resetting the pump and its parameters.

Data transmission from a continuous sensor is automatic, and transmissions are expected to occur at fixed time intervals. In addition, the distance between the sensor and the MedMon is expected to remain relatively constant as well as their relative position. Therefore, RSSI, DTOA, and AOA can be used to ascertain if there are physical anomalies pertaining to the data transmissions from the continuous sensor. In addition to these physical indicators, it is possible to specify acceptable ranges for the glucose level and its rate of change in the security policies as examples of behavioral security policies.

The security policies that we used in the example shown in FIG. 6a are shown in Table IV.

TABLE IV

Implemented security policies for the insulin delivery system

| Device | Anomaly | Response |
| --- | --- | --- |
| Remote control | Always | Jam |
| Glucose meter | Always | Raise warning |
| Continuous sensor | RSSI is greater than $A_h$ or smaller than $A_l$ | Raise warning |
|  | DTOA is greater than $\Delta t_h$ or smaller than $\Delta t_l$ | Raise warning |
|  | Glucose level is greater than $G_h$ or smaller than $G_l$ | Raise warning |
|  | Rate of change of glucose level is greater than $r_{th}$ or smaller than $-r_{th}$ | Raise warning |

Evaluation

Various results are presented and demonstrate the effectiveness of the MedMon in detecting and averting security attacks on the glucose monitoring and insulin delivery system.

Attack Detection and Reaction

The effectiveness of the MedMon is predicated upon its ability to detect and block anomalous transmissions before they can successfully reach the target device, which in our case is the insulin pump. To test this ability, the MedMon was set to the active mode. The attacker was configured to send command packets at random times, from varying locations, and at varying power levels. For this experiment, the MedMon was programmed to determine the command type, verify the device PIN in the packet against the stored PIN(s) of devices to which the insulin pump will respond, and if a match is found, raise a warning and jam the signal to disrupt the packet from being successfully received by the insulin pump. For the studied system, the transmission of all information bits in a packet (excluding synchronization bits) takes about 2.5 ms. As the device PIN is embedded in the middle of each incoming packet, the MedMon has enough information to decide whether to start jamming after receiving 65% of the packet. To enable quick reaction, the Med- Mon transmitter that transmits the jamming signal is always on, but its signal strength is kept at zero by default. This way, the transmitter does not need to be initiated when the jamming starts. Instead, only a command to set the signal strength is needed. The reaction latency of the MedMon is therefore only constrained by the processing delay for matching the parsed PIN with the stored PIN. As shown below in FIGS. 7a and 7b, the MedMon was able to successfully meet the latency constraint.

As noted earlier, the latency of transferring samples to the host over USB dominates the MedMon reaction latency. However, this overhead will be eliminated in an integrated implementation of the MedMon. Furthermore, performing even complex computations for anomaly detection should not be a bottleneck in a hardware implementation.

Figure 7A:
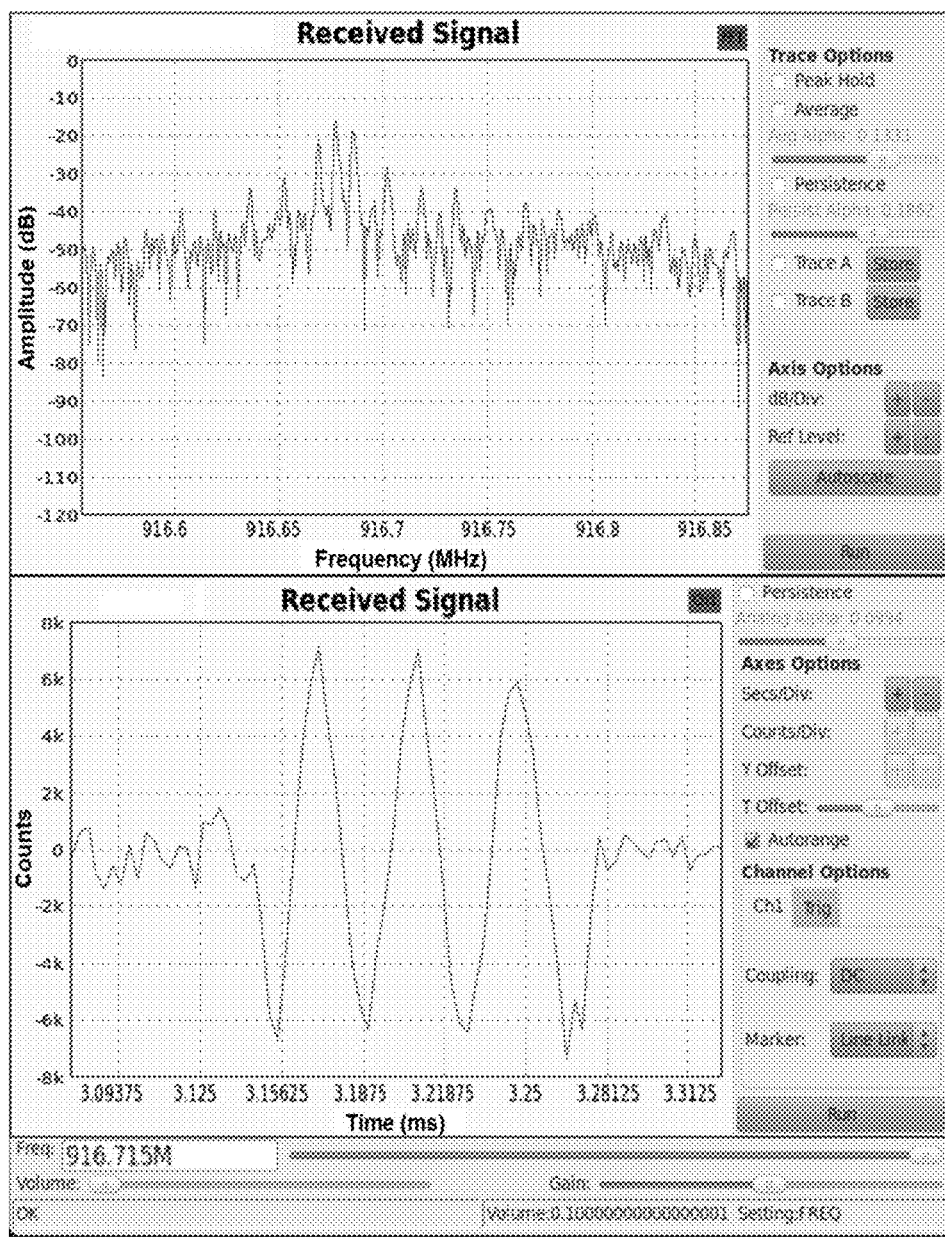
FIG. 7a is a graph of the frequency and time domains signals when the MedMon is in passive mode.
Figure 7B:
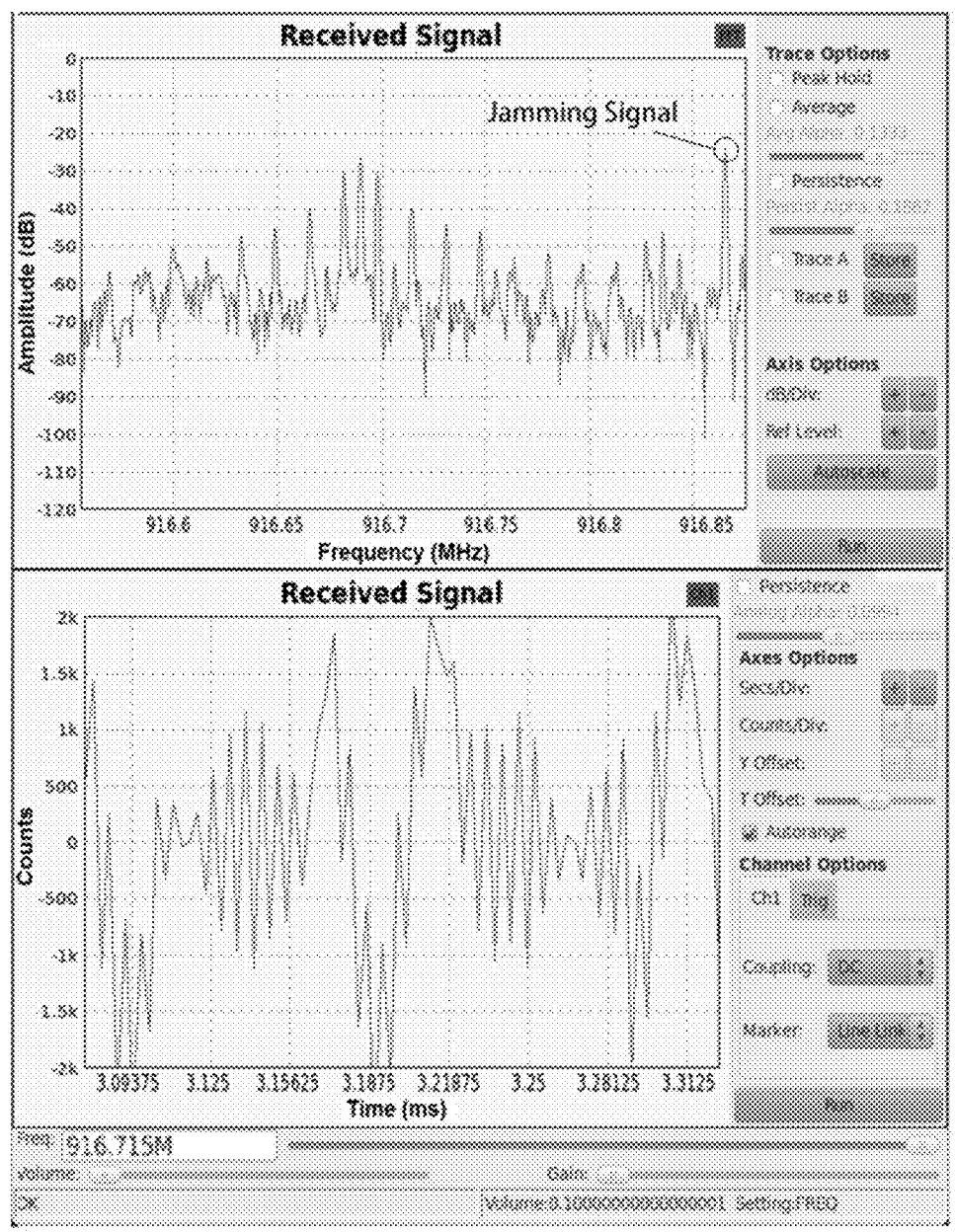
FIG. 7b is a graph of the frequency and time domains signals when the MedMon is in active mode.

FIG. 7a shows the frequency spectrum and time domain waveform of a command packet before the MedMon starts jamming. As can be seen from the spectrum (the upper graph), packet transmission is concentrated at around 916.68 MHz. Data are modulated with on-off keying, as shown in the lower graph. FIG. 7b shows the spectrum and waveform after jamming starts. The upper graph shows the jamming signal frequency is approximately 916.87 MHz, slightly higher than that of the command packet. As shown in the lower graph, the command packet is disrupted by the jamming signal. Note that the jamming signal frequency is adjustable.

Although not shown in FIGS. 7a and 7b, it was verified that warnings were also generated by the MedMon (in the example implementation, these messages are displayed on the screen of the host computer to which the USRP emulating the MedMon, is connected).

In these experiments, the MedMon successfully detected and jammed all command packets, achieving a 100% detection rate (0% false negatives). The jamming was always in time such that the insulin pump no longer responded to the remote control commands. One factor that contributed to the success of jamming in these experiments is the slow response of the insulin pump. It is believed that the receiver on the insulin pump is turned on and off periodically in order to save power. As a result, it was necessary to press the remote control button (resulting in repeated command packet transmissions from the remote control to the insulin pump) for more than a half second before the command can be recognized by the pump. The MedMon, which snoops on the communication at all times, easily beat the insulin pump in response time. However, as described previously, the MedMon can be designed to finish parsing and start jamming before receiving the entirety of a single packet.

As discussed above, all legitimate user commands from the remote control are jammed as well. The patient must disable jamming (or turn off the MedMon) before sending legitimate commands and enable jamming (or turn on the MedMon) afterwards.

Parameter Determination

Before the MedMon can be put to use, it must first be trained to learn or be manually programmed with the physical characteristics of the communications between the medical devices. Such characteristics may be stored as parameters in the MedMon memory, e.g., processor/memory 21 in FIG. 2. For example, by observing the communications between the medical devices under normal operations (in a safe physical environment), the MedMon can determine the RSSI thresholds to be used in anomaly detection.

To simulate the RSSI training for the continuous sensor, the remote control may act as the continuous sensor and initiate transmissions at various distances up to 20 cm away from the MedMon (considered a normal operating distance for a continuous sensor). After the training, the MedMon determined that the acceptable range of RSSI to be [800, 1400], i.e., $A_h$=1400 and $A_l$=800. This parameter is then stored in the MedMon memory.

Figure 8:
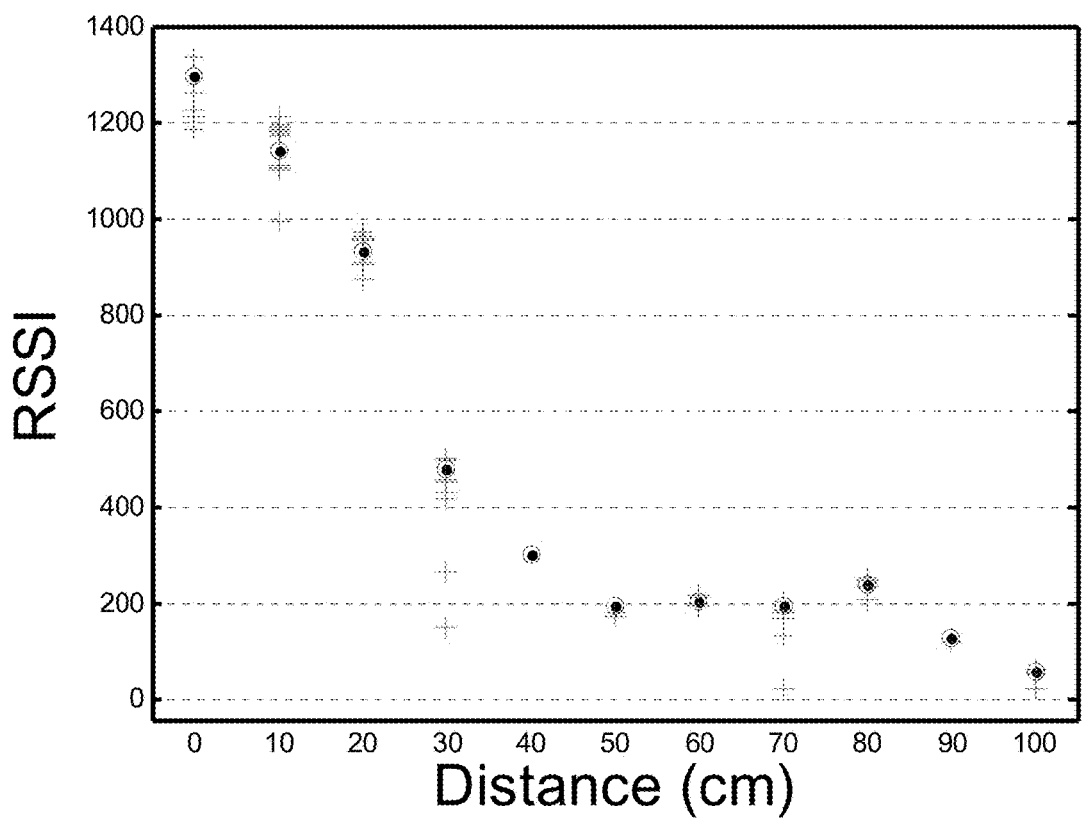
FIG. 8 is a graph showing the average received signal strengths as distance increases.

FIG. 8 is a graph showing the average received signal strengths as distance increases. In order to demonstrate that RSSI can be used for anomaly detection, the measured strengths of signals sent from various distances were recorded. FIG. 8 shows that RSSI decreases as the remote control moves further away from the MedMon. Each cross in FIG. 8 is an average signal strength of one received packet. Each circled dot represents the median signal strength of 168 packets collected at that distance.

Meanwhile, since every transmission from the glucose sensor is expected 60 seconds after the last one, the acceptable range of DTOA was set to be [59,61], i.e., $\Delta t_h$=61 and $\Delta t_l$=59. The parameter is also stored in the MedMon memory. The beginning of a transmission is recognized upon the first verification of the transmitter's device PIN. The current transmission is deemed to be complete only when consecutive zeros are received.

The experimental setup precluded the use of AOA since it has only one receiving antenna. It is conservatively assumed a 60° acceptable range for incoming continuous sensor signals, since the position of the continuous glucose sensor usually remains stable with respect to the insulin pump and the MedMon.

Physical Anomaly Detection

Once the MedMon was trained and the physical characteristics that the MedMon expects from incoming packets was specified. It was then possible to evaluate the effectiveness of physical anomaly detection. The MedMon was set to the passive mode and placed at a fixed position in an empty room. The attacker was configured to transmit attack signals at random times and various power levels, with changing distances and angles with respect to the MedMon.

Figure 9:
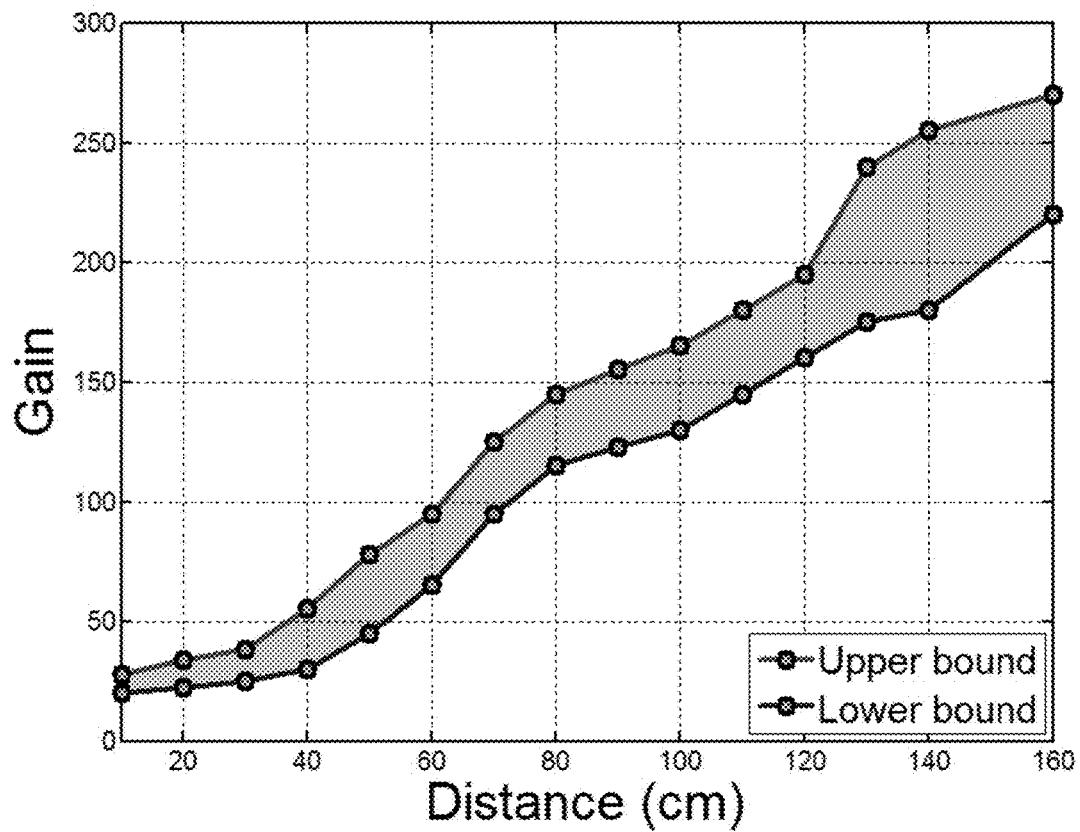
FIG. 9 is a graph showing transmission power levels that result in successful attacks for different distances with the MedMon using only RSSI for detection.
Figure 10:
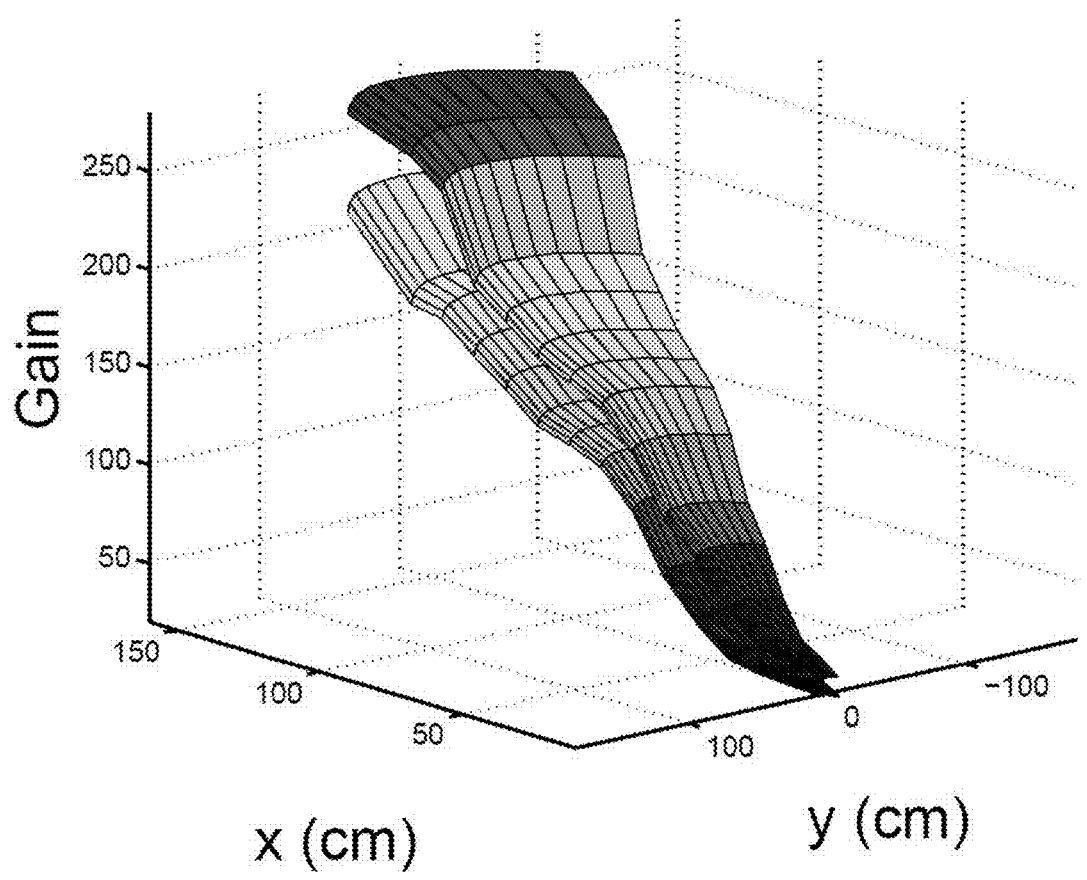
FIG. 10 is a graph showing successful attack transmission power levels and locations when the MedMon uses RSSI and AOA.

FIG. 9 shows the range of attacker transmission power that results in successful attacks at different distances from the MedMon. Power levels that fall outside the boundaries lead to unacceptable RSSI as measured by the MedMon. FIG. 10 further includes the AOA constraint and shows the transmission power for successful attacks at different spots on the horizontal plane when the MedMon is fixed at location (0, 0).

Over 250 attacks were performed with the following uniformly distributed ranges for various parameters: (i) signal amplification levels: 1-270×, (ii) distances: 10-270 cm, (iii) angles: −180-180°, and (iv) transmission intervals: 30-90 s. The MedMon raised warnings for all but two attacks, yielding a false negative rate (FNR) of less than 0.8%. It is important to note that the above measurements were performed in an empty room with no object near the transmitter/receiver or blocking the transmission paths. When a sizable object (e.g., a person) blocks the transmission path, the RSSI can drop by 10-20×. It would be quite challenging for the attacker to maintain the RSSI to within the required range in a changing channel environment with movement, obstructions, multi-path fading, etc. The RSSI of the transmissions from the glucose sensor was quite steady, since the MedMon and the sensor are positioned close to each other (both are carried or worn by the patient).

The false positive rate (FPR) was evaluated by narrowing the distance of the continuous glucose sensor to within 10-20 cm from the MedMon and initiating transmissions at 60 s intervals. In over 100 transmissions, zero false alarms were observed and thus a 0% FPR. AOA is not included in the evaluation of the FPR. It is believed that the false alarm induced by the 60° AOA limit is minimal, as the relative position of the MedMon and sensor vary minimally. However, the FPR may increase if the relative position and distance between the MedMon and sensor often change greatly, or if the transmission path is blocked. In that case, the security policies may be relaxed to reduce the FPR. However, that may cause the FNR to increase.

Behavioral Anomaly Detection

The evaluation of physical anomaly detection showed promising results for defending against naive attackers. However, after many trials, a sophisticated and diligent attacker may ascertain ranges of transmission parameters that lead to a high probability of success, breaking through the MedMon's physical protection layers. Fortunately, the MedMon can analyze the packet contents and capture "smart" attacks that are not caught by physical anomaly detection.

A behavioral anomaly detection module was implemented based on the security policies listed in Table IV above. $G_l$ and $G_h$ were set, respectively, to 70 and 140 mg/dL, which denote the normal range of glucose levels. $r_{th}$ was set to 5 mg/dL/min, which limits the maximum rate of change in the glucose level. When an abnormal glucose level ($<G_l$ or $>G_h$) or a drastic change ($>r_{th}$) was detected, the MedMon issued a warning. The behavioral anomaly may indicate an attack or a genuine sign of deteriorating glucose levels regarding which the patient should be alerted.

While the behavioral security policies described above are highly effective at detecting attacks that attempt to send grossly incorrect information to the insulin pump, it is possible that they could fail to detect attacks that are seemingly benign, e.g., attacks that slightly perturb the reported blood glucose levels. Such attacks do not immediately jeopardize the patient's health, but their accumulated effect could be harmful if the attack goes undetected for a long time. Security policies defined over long timescales can be introduced to further minimize the potential harm of such large-timescale attacks.

CONCLUSION

Many IWMDs perform life-sustaining functions, such as cardiac pacing and defibrillation, neuromodulation, and insulin delivery and administration. They are also responsible for monitoring, recording, and storing private patient information, and making changes in response to doctors' orders. Because of the critical nature of their functionality and the fact that many implanted devices are in close contact with human organs, safety concerns must be addressed aggressively and proactively. Changes made to these devices must correspond to doctors' orders to ensure delivery of the intended therapy. Any security compromise can be life-threatening.

This disclosure describes a MedMon, a non-invasive defense framework based on anomaly detection that guards against RF wireless attacks on PHSs. This defense solution is directed at enhancing the security of existing medical devices that are already deployed or upcoming products that cannot be easily modified. The MedMon snoops on all RF wireless communications to/from medical devices and uses multi-layered anomaly detection to identify potentially malicious transactions. Two layers of anomaly detection are disclosed: physical and behavioral. Physical anomaly detection targets the physical characteristics of the communications (packets) whereas behavioral anomaly detection targets the underlying information embedded in the communications.

The feasibility and effectiveness of the MedMon are demonstrated through a prototype implementation for an insulin delivery system using off-the-shelf devices. Experimental results indicate that the MedMon was able to thwart virtually all "naive" attacks using physical anomaly detection. Although a sophisticated attacker may evade physical anomaly detection by adapting the attacks, the most dangerous kinds of smart attacks can be captured by leveraging behavioral anomaly detection.

Besides the demonstrated insulin delivery system, the MedMon can be applied to other PHSs in which the sensor, controller, and actuator are wirelessly linked, such as cardiac pacing, defibrillation, insulin delivery and glucose monitoring, deep brain stimulation, intrathecal drug infusion, and many other diagnostic, monitoring, and therapeutic functions. The MedMon is more suitable for communication links that are not protected by cryptographic methods.

A highly desirable attribute of MedMon is that it incurs zero power overhead on the medical devices themselves, and it can be realized in a form factor that is not subject to the stringent power constraints associated with medical devices. For example, MedMon can be implemented as an add-on to a smartphone and provides an effective approach to enhancing the security of currently deployed PHSs.

It should be understood that many variations are possible based on the disclosure herein. Although features and elements are described above in particular combinations, each feature or element can be used alone without the other features and elements or in various combinations with or without other features and elements. The methods or flow charts provided herein may be implemented in a computer program, software, or firmware incorporated in a computer-readable (non-transitory) storage medium for execution by a general-purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general-purpose processor, a special purpose processor, a conventional processor, a digital signal processor (DSP), a plurality of microprocessors, one or more microprocessors in association with a DSP core, a controller, a microcontroller, Application-Specific Integrated Circuits (ASICs), Field-Programmable Gate Arrays (FPGAs) circuits, any other type of integrated circuit (IC), and/or a state machine.

What is claimed is:

1. A medical device monitor (MedMon) configured to operate in a system having communications between a first medical device associated with a patient and a second device, the MedMon comprising:

a unitary device comprising a receiver, an anomaly detector and a response generator;

the receiver being configured to monitor communications between the first medical device and second device;

the anomaly detector being configured to detect physical anomalies in a transmitted signal and behavioral anomalies in underlying medical information contained in the transmitted signal by analyzing the communications between the first medical device and second device for compliance with a set of security policies, the security policies defining allowable thresholds of both physical characteristics of the transmitted signal and underlying physiological data of the patient; and the response generator being configured to generate a response on a condition that an anomaly is detected.

2. The MedMon of claim 1, wherein the response is a warning message configured to warn the patient.

3. The MedMon of claim 1, further comprising a transmitter configured to transmit the response.

4. The MedMon of claim 3, wherein the response is a jamming signal configured to disrupt communications between the first medical device and second device.

5. The MedMon of claim 1, wherein the physical characteristics of the transmitted signal comprise at least one of: signal strength indicator (RSSI), time of arrival (TOA), differential time of arrival (DTOA), and angle of arrival (AOA).

6. The MedMon of claim 1, wherein each security policy is associated with a specific anomaly and has an associated response that is selected on a condition that the specific anomaly is detected.

7. The MedMon of claim 1, wherein the behavioral anomalies comprise at least one of repeated dosage commands and forged data that feign sudden changes in vital signs.

8. The MedMon of claim 1, wherein the allowable thresholds of the underlying physiological data of the patient are based on at least one of a historical record stored in a memory and predetermined value ranges programmed into the Medmon.

9. A method of monitoring communications between a first medical device associated with a patient and a second device, the method comprising:
   snooping on communications between the first medical device and second device;
   analyzing the communications between the first medical device and second device by detecting at least one physical anomaly based on compliance with a first set of security policies defining allowable thresholds of physical characteristics of a transmitted signal;
   analyzing the communications between the first medical device and second device by detecting at least one behavioral anomaly based on compliance with a second set of security policies defining allowable thresholds of underlying physiological data of the patient contained in the transmitted signal; and
   generating a response on a condition that an anomaly is detected.

10. The method of claim 9, wherein the response is a warning message configured to warn the patient.

11. The method of claim 9, further comprising transmitting the response.

12. The method of claim 11, wherein the response is a jamming signal configured to disrupt communications between the first medical device and second device.

13. The method of claim 9, wherein the physical characteristics of the transmitted signal comprise at least one of: signal strength indicator (RSSI), time of arrival (TOA), differential time of arrival (DTOA), and angle of arrival (AOA).

14. The method of claim 9, wherein each security policy is associated with a specific anomaly and has an associated response that is selected on a condition that the specific anomaly is detected.

15. The method of claim 9, wherein the behavioral anomalies comprise at least one of repeated dosage commands and forged data that feign sudden changes in vital signs.

16. The method of claim 9, wherein the allowable thresholds of the underlying physiological data of the patient are based on at least one of a historical record and predetermined value ranges.

17. A non-transitory computer-readable medium having stored thereon a computer program for execution by a processor configured to perform method of monitoring communications between a first medical device associated with a patient and a second device, the method comprising:
   snooping on communications between the first medical device and second device;
   analyzing the communications between the first medical device and second device by detecting at least one physical anomaly based on compliance with a first set of security policies defining allowable thresholds of physical characteristics of a transmitted signal;
   analyzing the communications between the first medical device and second device by detecting at least one behavioral anomaly based on compliance with a second set of security policies defining allowable thresholds of underlying physiological data of the patient contained in the transmitted signal; and
   generating a response on a condition that an anomaly is detected.

18. The computer-readable medium of claim 17, wherein the response is a warning message configured to warn the patient.

19. The computer-readable medium of claim 17, wherein the response is a jamming signal configured to disrupt communications between the first medical device and second device.

20. The computer-readable medium of claim 17, wherein the physical characteristics of the transmitted signal comprise at least one of: signal strength indicator (RSSI), time of arrival (TOA), differential time of arrival (DTOA), and angle of arrival (AOA).

21. The computer-readable medium of claim 17, wherein the behavioral anomalies comprise at least one of repeated dosage commands and forged data that feign sudden changes in vital signs.

* * * * *